(12) United States Patent
Zhang et al.

(10) Patent No.: US 10,517,937 B2
(45) Date of Patent: Dec. 31, 2019

(54) IMMUNOTHERAPY FOR THE TREATMENT OF CANCER

(71) Applicant: University Health Network, Toronto (CA)

(72) Inventors: Li Zhang, Toronto (CA); Jong Bok Lee, Toronto (CA); Branson Chen, Toronto (CA)

(73) Assignee: University Health Network, Toronto, ON (CA)

( * ) Notice: Subject to any disclaimer, the term of this patent is extended or adjusted under 35 U.S.C. 154(b) by 121 days.

(21) Appl. No.: 15/503,916

(22) PCT Filed: Aug. 17, 2015

(86) PCT No.: PCT/CA2015/050780
§ 371 (c)(1),
(2) Date: Feb. 14, 2017

(87) PCT Pub. No.: WO2016/023134
PCT Pub. Date: Feb. 18, 2016

(65) Prior Publication Data
US 2017/0274060 A1    Sep. 28, 2017

Related U.S. Application Data

(60) Provisional application No. 62/037,889, filed on Aug. 15, 2014.

(51) Int. Cl.
| | | |
|---|---|---|
| A61K 35/17 | (2015.01) | |
| A61K 39/00 | (2006.01) | |
| A61K 31/7068 | (2006.01) | |

(52) U.S. Cl.
CPC ...... *A61K 39/0011* (2013.01); *A61K 31/7068* (2013.01); *A61K 35/17* (2013.01); *A61K 2039/5158* (2013.01)

(58) Field of Classification Search
CPC .......................... A61K 39/0011; A61K 35/17
USPC ...................................................... 424/277.1
See application file for complete search history.

(56) References Cited

U.S. PATENT DOCUMENTS

| 6,953,576 B2 | 10/2005 | Zhang | |
| 10,201,572 B2 * | 2/2019 | Zhang | A61K 35/17 |

FOREIGN PATENT DOCUMENTS

| WO | WO2007056854 A1 | 5/2007 |
| WO | WO 2009/097140 A1 | 8/2009 |
| WO | WO 2016/179684 A1 | 11/2016 |

OTHER PUBLICATIONS

Pigneux et al. (Experimental Hematology 2008, 36: 1648-1659).*
Menzin, J., et al., "The outcomes and costs of acute myeloid leukemia among the elderly." Arch Intern Med., 2002, vol. 162, pp. 1597-1603.
Ungewickell, A., and Medeiros, B.C., "Novel agents in acute myeloid leukemia." Int J Hematol., 2012, vol. 96, pp. 178-185.
Hoang, V.T., et al., "Identification of leukemia stem cells in acute myeloid leukemia and their clinical relevance." Biotechnol J., 2012, 7, pp. 779-788.
Bucisano, F., et al., "Prognostic and therapeutic implications of minimal residual disease detection in acute myeloid leukemia." Blood, 2012, vol. 119, No. 2, pp. 332-341.
Ferrara, F., et al., "Prognostic factors and therapeutic options for relapsed or refractory acute myeloid leukemia." Haematologica, 2004, 89 (8), pp. 998-1008.
Garces-Eisele, J., "Molecular biology strategies to detect residual disease." Hematology, 2012, vol. 17, Suppl 1: S66-8.
Lin, T.L. and Levy, M.Y., "Acute myeloid leukemia: focus on novel therapeutic strategies." Clin Med Insights Oncol., 2012, 6, pp. 205-217.
Ishizawa, K., et al., "Tumor-initiating cells are rare in many human tumors." Cell Stem Cell., 2010, 7(3), pp. 279-282.
Kadowaki, N., and Kitawaki, T., "Recent advance in antigen-specific immunotherapy for acute myeloid leukemia." Clin Dev Immunol., 2011, Article ID 104926, 7 pages.
Vaz, A.P., et al., "Cancer stem cells and therapeutic targets: an emerging field for cancer treatment." Drug Deliv Transl Res., 2013, 3(2), pp. 113-120.
Alatrash, G., and Molldrem, J.J., "Immunotherapy of AML." Cancer Treatment and Research, 2009, 145, pp. 237-255.
Shlomchik, W.D., "Graft-versus-host disease." Nat Rev Immunol., 2007, vol. 7, pp. 340-352.
Rosenberg, S.A., et al., "Use of tumor-infiltrating lymphocytes and interleukin-2 in the immunotherapy of patients with metastatic melanoma. A preliminary report." N Engl J Med., 1988, 319, pp. 1676-1680.
Teague, R.M., and Kline, J., "Immune evasion in acute myeloid leukemia: current concepts and future directions." J Immunother Cancer., 2013, 1(13).
Kochenderfer, J.N., et al., "Adoptive transfer of syngeneic T cells transduced with a chimeric antigen receptor that recognizes murine CD19 can eradicate lymphoma and normal B cells." Blood, 2010, vol. 116, No. 19, pp. 3875-3886.
Johnson, L.A., et al., "Gene therapy with human and mouse T-cell receptors mediates cancer regression and targets normal tissues expressing cognate antigen." Blood, 2009, vol. 114, No. 3, pp. 535-546.
Parkhurst, M.R., et al., "T cells targeting carcinoembryonic antigen can mediate regression of metastatic colorectal cancer but induce severe transient colitis." Mol Ther., 2011, vol. 19, No. 3, pp. 620-626.
Robbins, P.F., et al., "Tumor regression in patients with metastatic synovial cell sarcoma and melanoma using genetically engineered lymphocytes reactive with NY-ESO-1." J Clin Oncol., 2011, vol. 29, No. 7, pp. 917-924.

(Continued)

*Primary Examiner* — Yan Xiao
(74) *Attorney, Agent, or Firm* — Bereskin & Parr LLP/S.E.N.C.R.L., s.r.l.; I. Laurence MacPhie

(57) ABSTRACT

Methods for the treatment of cancer using double negative (DN) T cells are described. The DNTs may be used for the treatment of chemotherapy-resistant cancers such as recurring or relapsing acute myeloid leukemia (AML). The use of allogenic DNTs, such as those derived from healthy donors, that do not exhibit toxicity towards normal host tissues and the complications associated with graft-versus-host-disease, is also described.

20 Claims, 14 Drawing Sheets

(56) References Cited

OTHER PUBLICATIONS

Peinert, S., et al. "Gene-modified T cells as immunotherapy for multiple myeloma and acute myeloid leukemia expressing the Lewis Y antigen." Gene Ther., 2010, 17, pp. 678-686.

Xue, S.A., et al., "Development of a Wilms' tumor antigen-specific T-cell receptor for clinical trials: engineered patient's T cells can eliminate autologous leukemia blasts in NOD/SCID mice." Haematologica., 2010, 95, pp. 126-134.

Brentjens, R., et al., "Treatment of chronic lymphocytic leukemia with genetically targeted autologous T cells: case report of an unforeseen adverse event in a phase I clinical trial." Mol Ther., 2010, vol. 18, No. 4, pp. 666-668.

Zhang, Z.X., et al., "Identification of a previously unknown antigen-specific regulatory T cell and its mechanism of suppression." Nat Med., 2000, vol. 6, No. 7, pp. 782-789.

Young, K.J., et al., "Antitumor activity mediated by double-negative T cells." Cancer Res., 2003, 63, pp. 8014-8021. (A).

Merims, S., et al., "Anti-leukemia effect of ex vivo expanded DNT cells from AML patients: a potential novel autologous T-cell adoptive immunotherapy." Leukemia, 2011, 25(9), pp. 1415-1422. (A).

Young, K.J., et al., "Inhibition of graft-versus-host disease by double-negative regulatory T cells." J Immunol., 2003, 171, pp. 134-141. (B).

He, K.M., et al., "Donor double-negative Treg promote allogeneic mixed chimerism and tolerance." Eur J Immunol., 2007, 37, pp. 3455-3466.

Mciver, Z., et al., "Double-negative regulatory T cells induce allotolerance when expanded after allogeneic haematopoietic stem cell transplantation." Br J Haematol., 2008, 141, pp. 170-178.

Fontaine, P., et al., "Adoptive transfer of minor histocompatibility antigen-specific T lymphocytes eradicates leukemia cells without causing graft-versus-host disease." Nat Med., 2001, vol. 7, No. 7, pp. 789-794.

Barabe, F., et al., "Modeling the initiation and progression of human acute leukemia in mice." Science, 2007, vol. 316, pp. 600-604.

Ali, N., et al., "Xenogeneic graft-versus-host-disease in NOD-scid IL-2Ry null mice display a T-effector memory phenotype." PLoS One, 2012, vol. 7, Issue 8, e44219.

Merims, S., et al., "Human Vδ1-T cells regulate immune responses by targeting autologous immature dendritic cells." Hum. Immunol., 2011, 72, pp. 32-36. (B).

Kenderian, S.S., et al., "CD33-specific chimeric antigen receptor T cells exhibit potent preclinical activity against human acute myeloid leukemia." Leukemia, 2015, 29(8), pp. 1637-1647, doi:10.1038/leu.2015.52.

Lichtenegger, F.S., et al., "Immunotherapy for Acute Myeloid Leukemia." Semin Hematol., 2015, vol. 52, Issue 3, pp. 207-214, doi:10.1053/j.seminhematol.2015.03.006.

Tettamanti, S., et al., "CD123 AML targeting by chimeric antigen receptors: A novel magic bullet for AML therapeutics?" Oncoimmunology, 2014, 3, e28835, doi:10.4161/onci.28835.

Wang, Q.S., et al., "Treatment of CD33-directed chimeric antigen receptor-modified T cells in one patient with relapsed and refractory acute myeloid leukemia." Mol Ther., 2015, vol. 23, No. 1, pp. 184-191, doi:10.1038/mt.2014.164.

Arpinati, M., and Curti, A., "Immunotherapy in acute myeloid leukemia." Immunotherapy, 2014, vol. 6, No. 1, pp. 95-106, doi:10.2217/imt.13.152.

Campbell, K.S., and Hasegawa, J., "Natural killer cell biology: an update and future directions." The Journal of allergy and clinical immunology, 2013, 132(3), pp. 536-544, doi:10.1016/j.jaci.2013.07.006.

Ruggeri, L. et al. "Effectiveness of donor natural killer cell alloreactivity in mismatched hematopoietic transplants." Science, 2002, vol. 295, pp. 2097-2100, doi:10.1126/science.1068440.

June, C.H., "Adoptive T cell therapy for cancer in the clinic." Journal of Clinical Investigation, 2007, vol. 117, No. 6, pp. 1466-1476.

Hourigan, C.S., and Karp, J.E., "Minimal residual disease in acute myeloid leukaemia." Nat Rev Clin Oncol., 2013, vol. 10, pp. 460-471, doi:10.1038/nrclinonc.2013.100.

Brissot, E., and Mohty, M., "Which Acute Myeloid Leukemia Patients Should Be Offered Transplantation?" Semin Hematol., 2015, vol. 52, No. 3, pp. 223-231, doi:10.1053/j.seminhematol.2015.03.001.

Vyas, P., et al., "Reprint of: Allogeneic hematopoietic cell transplantation for acute myeloid leukemia." Biol Blood Marrow Transplant, 2015, vol. 21, Issue 2, S3-10, doi:10.1016/j.bbmt.2014.12.032.

MacDonald, K.P., et al., "Biology of graft-versus-host responses: recent insights." Biol Blood Marrow Transplant, 2013, 19, S10-14, doi:10.1016/j.bbmt.2012.11.005.

McDermott, S.P., et al., "Comparison of human cord blood engraftment between immunocompromised mouse strains." Blood, 2010, vol. 116, No. 2, pp. 193-200, doi:10.1182/blood-2010-02-271841.

Drake, A.C., et al., "Human CD34+ CD133+ hematopoietic stem cells cultured with growth factors including Angptl5 efficiently engraft adult NOD-SCID Il2rgamma-/- (NSG) mice." PLoS One, 2011, vol. 6, Issue 4, e18382, doi:10.1371/journal.pone.0018382.

Covassin, L., et al., "Human peripheral blood CD4 T cell-engrafted non-obese diabetic-scid IL2rgamma(null) H2-Ab1 (tm1Gru) Tg (human leucocyte antigen D-related 4) mice: a mouse model of human allogeneic graft-versus-host disease." Clin Exp Immunol., 2011, 166, pp. 269-280, doi:10.1111/j.1365-2249.2011.04462.

Wilhelm, M., et al., "Successful adoptive transfer and in vivo expansion of haploidentical γδ T cells." J Trans Med., Feb. 15, 2014, vol. 12:45.

Li, X. et al., "In vivo characterization of human double negative T cells as a potential novel immunotherapy for AML." Cytotherapy, 2013, vol. 15, p. S41. (Abstract).

Zhang, L. et al., "Novel immunotherapy for AML using DNT cells (P4348)." The Journal of Immunology, 2013, 190, 177.7 (Abstract).

International Search Report completed Oct. 20, 2015 and Written Opinion completed Oct. 20, 2015 for corresponding PCT Application No. PCT/CA2015/050780.

Lamb, L.S., et al., "Graft-versus-leukaemia. Human γδ+ T lymphocytes have in vitro graft vs. leukemia activity in the absence of an allogeneic response." Bone Marrow Transplantation, 2001, 27, pp. 601-606.

Juvet, S.C., and Zhang, L., "Double negative regulatory T cells in transplantation and autoimmunity: recent progress and future directions." Journal of Molecular Cell Biology, 2012, vol. 4, No. 1, 48-58.

Hillhouse, E.E., et al., "Immunoregulatory CD4-CD8- T cells as a potential therapeutic tool for transplantation, autoimmunity, and cancer." Frontiers in Immunology, Jan. 2013, vol. 4, Article 6, 1-10.

Lee, J.B., et al., "Allogeneic Human Double Negative T Cells as a Novel Immunotherapy for Acute Myeloid Leukemia and Its Underlying Mechanisms." Clinical Cancer Research, 2017, OF1-OF13.

Lee, J.B., et al., "Efficacy and Safety of Allogeneic Double Negative T Cell as a Cellular Therapy for AML and Its Underlying Mechanism." Blood Journal, 2015, 1-5.

Anonymous, "Study of Allogeneic Double Negative T Cells (DNT-UHN-1) in Patients With High Risk Acute Myeloid Leukemia." ClinicalTrials.gov.

Supplementary European Search Report completed Feb. 5, 2018 for corresponding European Patent Application No. 15 83 2624.

Barrett, A.J., and Le Blanc, K., "Immunotherapy prospects for acute myeloid leukaemia." Clinical and Experimental Immunology, 2010, 161(2), p. 223-232.

Smits, E., et al., "Immunotherapy of Acute Myeloid Leukemia: Current Approaches." The Oncologist, 2009, 14, p. 240-252.

\* cited by examiner a)

IMMUNOTHERAPY FOR THE TREATMENT OF CANCER

CROSS REFERENCE TO RELATED APPLICATIONS

This Application is a national phase entry of PCT/CA2015/050780 filed Aug. 17, 2015 (which designates the U.S.) which claims priority to U.S. Provisional Patent Application No. 62/037,889 filed Aug. 15, 2014 (now abandoned), the contents of which are incorporated by reference herein in their entirety.

FIELD OF THE INVENTION

The disclosure relates to the treatment of cancer such as leukemia and lymphoma, including acute myeloid leukemia (AML) using double negative T cells.

BACKGROUND OF THE INVENTION

Acute myeloid leukemia (AML) is the leading cause of adult acute leukemia and accounts for ~80% of all adult leukemia (Menzin et al., 2002). Despite the extensive research done to develop more effective ways of targeting the disease, AML is associated with low long-term survival; only ~5% of elderly patients and ~30% younger patients with AML manage to survive for 5 years or longer (Ungewickell and Medeiros, 2012; Hoand et al., 2012). Conventional chemotherapy can effectively achieve initial remission of the disease in >70% of the treated AML patients (Ungewickell and Medeiros, 2012). However, due to the highly heterogeneous nature of the disease, ~30% of AML patients do not respond to chemotherapy (Ungewickell and Medeiros, 2012; Bucisano et al., 2012). Furthermore, chemotherapy fails to achieve complete clearance of the disease in most patients, and more than 70% of patients in remission suffer from relapsing AML within 2 years after the initial treatment (Ungewickell and Medeiros, 2012; Bucisano et al., 2012). There is no standard treatment regime for patients with relapsing AML, which is associated with poor prognosis (Ferrara et al., 2004). Relapsing AML is caused by a phenomenon called minimal residual disease (MRD), which is mediated by an AML cell population with resistance to chemotherapy (Garces-Eisele, 2012; Lin and Levy, 2012). It is known that MRD is largely contributed by leukemic stem cell (LSC) population, as it has the ability to withstand harsh environment and conditions, such as chemotherapy (Ishikawa et al., 2010; Kadowaki and Kitawaki, 2011; Vaz et al., 2013). Therefore, development of treatments to target AML-LSC and MRD to achieve relapse-free clearance of the disease has been an active area of research.

Allogeneic hematopoetic stem cell transplantation (allo-HSCT) is a potential curative treatment for AML patients and is associated with higher disease-free survival rates than conventional chemotherapy (Alatrash and Molldrem, 2009). Donor-derived T cell mediated anti-leukemic effects contribute to the increased survival in patients, as T cell depleted grafts result in higher relapse rates (Alatrash and Molldrem, 2009). However, the use of allo-HSCT in the clinic is limited by a shortage of suitable donors, the toxicity of the treatment, and other associated complications (Alatrash and Molldrem, 2009; Shlomchik, 2007). Potent immune responses can be induced on normal tissues, resulting in tissue damage and, possibly, in death of the patients in severe cases (Alatrash and Molldrem, 2009; Shlomchik, 2007) thus posing a major obstacle that limits the use of allogenic cellular therapies.

Since the early work on utilizing T cell immunotherapy to treat melanoma patients, significant progress has been made in adoptive T cell therapy for other cancers, which further supports the potential use of cellular therapies to achieve relapse-free AML clearance (Rosenberg et al., 1988). Antigens that are upregulated in leukemic cells, leukemia associated antigens (LAA), have been identified, and the anti-leukemic effect of LAA-specific T cells has been demonstrated in vitro and in animal models (Vaz et al, 2013; Teague and Kline, 2013). However, the use of LAA-specific T cells is hampered by difficulties in isolation and expansion of these cells (Kochenderfer et al., 2010; Johnson et al., 2009; Parkhurst et al., 2011; Robbins et al., 2011). Furthermore, even though many LAAs are over expressed in AML, expression of the antigens in other tissues such as thymus prevents development of mature T cells with receptors that have high avidity towards LAAs due to thymic selection of T cell specificity (Teague and Kline, 2013). Alternatively, attempts have been made to use transgenic CD8+ T cells expressing transgenic TCRs or chimeric Ag receptor against LAAs, such as Wilms' tumour antigen or Lewis Y, respectively (Peinert et al., 2010; Xue et al., 2010). These T cells have a significantly increased ability to bind to LAAs and show excellent anti-tumour activity (Kochenderfer et al., 2010; Johnson et al., 2009; Parkhurst et al., 2011; Robbins et al., 2011). However, the potential side-effects associated with gene therapy, together with complicated and long procedures, imposes limitations on using these strategies to treat AML. In addition, injecting supra-physiological numbers of genetically engineered T cells can lead to severe adverse events, including death. Thus, the development of new cellular immunotherapies with potent effects on a broad range of cancers without the requirement of identifying LAAs may revolutionize leukemia immunotherapy.

Double negative T cells (DN T cells or DNTs) are mature peripheral T lymphocytes that express the CD3-TCR complex but do not express CD4, CD8, or NKT cell markers αGalCer-loaded CD1d and Jα24-Vα14; they represent 1~3% of peripheral blood mononuclear cells (PBMC) in humans (Zhang et al., 2000). Protocols for expanding DNTs from AML patients during chemotherapy-induced complete remission have been described and AML patient DNTs have been shown to have significant anti-leukemic activity against the primary AML cells obtained from the same patient in vitro (Young et al., 2003; Merims et al., 2011).

Previously, DNTs have been shown to induce the killing of an allogeneic AML cell-line in a dose-dependent manner through the perforin-granzyme dependent pathway (Merims et al., 2011). In animal models, it has also been shown that unlike conventional CD4+ or CD8+ T cells, infusion of allogeneic mouse DNTs may confer immune inhibitory function (Zhang et al., 2000; Young et al., 2003; He et al., 2007). However, the activity of DNTs with respect to patient primary leukemic cells had not been studied in vivo.

SUMMARY OF THE INVENTION

In one aspect of the invention, it has been determined that double negative (DN) T cells (DNTs) are effective for the treatment of cancer such as lymphoma or leukemia. In particular, immunotherapy using DNTs has been demonstrated to be effective for the treatment of acute myeloid leukemia (AML), including killing of leukemic cells that are resistant to treatment with chemotherapy. Optionally, the DNTs may be autologous, such as DNTs from a subject with cancer or suspect of having cancer, or allogenic, such as DNTs from a healthy donor without cancer. Remarkably, DNTs were observed to have a cytotoxic effect on cancer cells in vitro and in vivo in xenograft models without detectable toxicity to normal cells and tissues.

As shown in Example 2, injected DNTs have been demonstrated to proliferate and persist in vivo and migrate to different tissues including blood, spleen and lung and populations of DNTs were also observed in lungs, liver and bone marrow, suggesting that DNTs may target tumors in these organs. The inventors have also demonstrated that allogenic DNTs from healthy donors selectively target AML cells and exhibit cancer killing activity. DNTs were also shown to inhibit engraftment in an AML xenograft model, showing that DNTs can reduce the level of leukemic cells in vivo. Furthermore, as shown in Example 6, injected DNTs migrate from the blood to the bone marrow and target pre-existing AML cancer cells, suggesting that DNTs can be effective in a clinical setting for treating subjects with AML.

A number of cancer cell lines were also demonstrated to exhibit a high level of susceptibility to DNT cell mediated cytotoxicity in vitro, including Daudi (B cell lymphoma (Burkitt's lymphoma)), Jurkat (acute T cell lymphoma), K562 (Chronic myeloid leukemia), U937 (Chronic myeloid leukemia) as well as primary and established lung cancer cell lines (data not shown).

Chemotherapy is the standard treatment used for patients with AML and can be effective at reducing the leukemia load and achieving initial remission of the disease. However, chemotherapy often fails to achieve complete clearance leading to a high rate of relapse in AML patients. The ability to eliminate AML cells that are non-responsive to chemotherapy and lower the relapse rate is therefore expected to significantly increase the survival of patients with AML. As shown in Example 7 the inventors have demonstrated that DNTs are effective in killing chemotherapy-resistant cancer cells and in particular chemotherapy-resistant AML. DNTs may therefore be useful for immunotherapy in subjects who do not respond to chemotherapy or to prevent or treat cases of relapsing or recurring cancers such as AML and/or chemotherapy-resistant minimal resistant disease (MRD).

In another aspect of the invention, DNTs have been shown to be effective for killing cancer cells in combination with a cell cycle inhibitor. As shown in Example 9, combination therapy using DNTs and the cell cycle inhibitor AraC lowered the level of AML engraftment relative to treatment with AraC alone.

As set out in Example 10, allogenic DNTs have a potent anti-leukemic effect against primary AML patient blasts, including chemotherapy-resistant cancer cells in vitro and in xenograft models without detectable toxicity to normal cells and tissues. Allogeneic DNTs were not observed to attack normal peripheral blood mononuclear cells (PBMC) or hematopoietic progenitor/stem cells, nor cause xenogeneic graft-versus-host disease in mice.

Accordingly, in one embodiment there is provided a method of treating cancer in a subject in need thereof, comprising administering to the subject an effective amount of DNTs as described herein. Also provided is the use of DNTs as described herein for the treatment of cancer in a subject in need thereof. In one embodiment, the cancer is leukemia. In a preferred embodiment, the cancer is acute myeloid leukemia (AML). In one embodiment, the cancer is chronic myeloid leukemia (CML). In one embodiment, the cancer is lymphoma. In one embodiment, the cancer is non-Hodgkin lymphoma (NHL). In one embodiment, the cancer is B cell lymphoma, such as Burkitt's lymphoma. In one embodiment, the cancer is acute T cell lymphoma. In one embodiment, the cancer is lung cancer.

In one embodiment, the cancer is resistant to treatment with chemotherapy. For example, in one embodiment the cancer is chemotherapy-resistant AML. In one embodiment, the methods and uses described herein are for the treatment of a subject with recurring or relapsing cancer. In one embodiment, the cancer is recurring, relapsing or refractory leukemia or lymphoma. In one embodiment, the cancer is relapsing cancer such as relapsing AML caused by minimal residual disease (MRD) or leukemic stem cells. In one embodiment, the subject is not in complete remission. For example, in one embodiment the subject has one or more detectable cancer cells, optionally one or more detectable leukemic or lymphoma cells. In one embodiment, the subject has previously undergone chemotherapeutic treatment for cancer but the cancer cells do not respond to the chemotherapy treatment (i.e. refractory cancer). In one embodiment, the subject has previously undergone chemotherapeutic treatment for cancer and has one or more detectable cancer cells. In one embodiment, the subject has not previously undergone chemotherapeutic treatment for cancer. In one embodiment, DNTs are for use or administration in a subject who has cancer or is suspected of having cancer who is not undergoing chemotherapy.

In one embodiment, there is provided a method for inhibiting the growth or proliferation of cancer cells comprising contacting the cancer cells with one or more DNTs. Also provided is the use of DNTs as described herein for inhibiting the growth or proliferation of cancer cells. Optionally, the cancer cells are in vivo or in vitro. In one embodiment, the cancer cells are leukemic cells. In a preferred embodiment, the cancer cells are AML cells. In one embodiment, the cancer cells are lymphoma cells. In one embodiment, the cancer cells are cells that are resistant to treatment with chemotherapy. For example, in one embodiment the cancer cells are AML cells that are resistant to treatment with a cell cycle inhibitor such as AraC. In one embodiment, the cancer cells are cancer stem cells, such as leukemic stem cells.

The DNTs described herein may be readily obtained by a person of skill in the art and are readily distinguished from other kinds of T cells. In one embodiment, the DNTs do not express CD4 and CD8. In one embodiment, the DNTs express CD3-TCR complex and do not express CD4 and CD8. In one embodiment, the DNTs have the phenotype CD3+, γδ-TCR+ or αβ-TcR+, CD4−, CD8−, α-Gal−, PD-1−, CTLA4−. In one embodiment, the DNTs have the phenotype CD3+, γδ-TCR+ or αβ-TcR+, CD4−, CD8−, α-Gal−, PD-1−, CTLA4−, CD44+, CD28−. In one embodiment, the DNTs have the phenotype CD3+, CD4−, CD8−, α-Gal−, PD-1−, CTLA4−, CD44+. In one embodiment, the DNTs have the phenotype CD3+, CD4−, CD8−, α-Gal−, Jα24−, Vα14−, CD44+, PD-1−, CTLA4−, CD45Ro+. In one embodiment, the DNTs may be obtained from a sample comprising peripheral blood mononuclear cells (PBMC). In one embodiment, the sample is a blood sample. Optionally, the sample is from a healthy donor or from a subject with cancer or suspected of having cancer and the DNTs are used to treat the subject.

Optionally, the DNT cells may be expanded in vitro or ex vivo before their administration or use for the treatment of cancer as described herein. In one embodiment, the DNTs are formulated for use or administered to the subject by intravenous injection.

In one embodiment, the DNTs are autologous DNTs obtained from a subject, such as a subject with cancer or suspected of having cancer. In one embodiment, the DNTs are from a subject with one or more detectable cancer cells, optionally one or more leukemic or lymphoma cells. In one embodiment, the DNTs are from a subject who has previously been treated for cancer. In one embodiment, the DNTs are from a subject in complete remission. In one embodiment, the DNTs are from a subject who is not in complete remission. In one embodiment, the DNTs are obtained from the subject prior to, during or after chemotherapy. For example, the DNTs may be obtained from a subject prior to starting a course of chemotherapy, after a first round of chemotherapy, between rounds of chemotherapy, or after one or more rounds of chemotherapy. In one embodiment, the DNTs are obtained from the subject the same day, within 3 days, within 1 week, within 2 weeks, within 3 weeks or within 1 month of the administration of a chemotherapeutic agent to the subject.

In one embodiment, the DNTs are allogenic, such as DNTs obtained from one or more subjects without cancer. In one embodiment, the DNTs are obtained from one or more healthy donors.

In one embodiment, the DNTs are for use or administration to a subject for the treatment of cancer, such as for the treatment of leukemia or lymphoma. In one embodiment, the DNTs are for use or administration to a subject who is not undergoing chemotherapy. In another embodiment, the DNTs are for use or administration to a subject prior to, during or after chemotherapy. For example, the DNTs may be for use or administration to a subject prior to starting a course of chemotherapy, after a first round of chemotherapy, between rounds of chemotherapy, or after one or more rounds of chemotherapy. In one embodiment, the DNTs are administered to the subject the same day, within 3 days, within 1 week, within 2 weeks, within 3 weeks or within 1 month of chemotherapy. In one embodiment, chemotherapy comprises the use or administration of one or more chemotherapeutic agents, such as cell cycle inhibitors as described herein.

Optionally, two or more separate doses of DNTs may be administered or used for the treatment of cancer in a subject in need thereof. For example, in one embodiment the methods and uses described herein include a first dose of DNTs and at least one additional dose of DNTs. In one embodiment, the at least one additional dose is for use or administration at least 3 days after the last dose of DNTs, at least 5 days after the last dose of DNTs, or optionally between 3 days and two weeks after the last dose of DNTs. In one embodiment, the two or more separate doses are for administration or use prior to, during or after chemotherapy.

In one embodiment, the DNTs are recombinant cells that have been modified to express one or more exogenous proteins. For example, in one embodiment, the DNTs described herein express a receptor with a high avidity to a cancer biomarker, such as a protein expressed on the surface of a cancer cell. In one embodiment, the DNTs express a Chimeric Antigen Receptor (CAR) that preferentially binds to a cancer cell, such as a leukemic cell. For example, in one embodiment the DNTs described herein express one or more receptors that bind to CD33, CD19, CD20, CD123 and/or LeY.

In one embodiment, the DNTs preferentially kill and/or inhibit the proliferation of cancer cells relative to normal cells. In one embodiment, the DNTs preferentially kill and/or inhibit the proliferation of leukemic cells relative to normal cells. For example, in one embodiment, the DNTs preferentially kill and/or inhibit the proliferation of AML blasts relative to other hematopoietic cells or peripheral blood mononuclear cells (PBMCs). In one embodiment, the DNTs preferentially kill and/or inhibit the proliferation of leukemic stem cells relative to normal hematopoietic stem cells.

In another embodiment, the DNTs do not cause an allogeneic immune response when used or administered to a subject for the treatment of cancer.

The inventors have determined that combination therapy using DNTs and a chemotherapeutic agent such as a cell cycle inhibitor is surprisingly effective at killing cancer cells and in particular AML. Accordingly, in one embodiment there is provided a method of treating cancer in a subject comprising administering to the subject an effective amount of DNTs and a chemotherapeutic agent. Also provided is the use of an effective amount of DNTs and a chemotherapeutic agent for the treatment of cancer. In one embodiment, the chemotherapeutic agent is a cell cycle inhibitor. In one embodiment, the cell cycle inhibitor is a DNA synthesis inhibitor. Optionally, the DNTs and the chemotherapeutic agent are administered to the subject at different times or at the same time.

In one embodiment, the chemotherapeutic agent is a cell cycle inhibitor. In one embodiment, the cell cycle inhibitor is a cell cycle dependent chemotherapy drug. Exemplary cell cycle inhibitors include, but are not limited to, Doxorubicin, Melphlan, Roscovitine, Mitomycin C, Hydroxyurea, 5Fluorouracil, Cisplatin, Ara-C, Etoposide, Gemcitabine, Bortezomib, Sunitinib, Sorafenib, Sodium Valproate, HDAC Inhibitors, or Dacarbazine. Examples of HDAC inhibitors include, but are not limited to, FR01228, Trichostatin A, SAHA and PDX101.

In one embodiment there is provided a method of treating acute myeloid leukemia (AML) in a subject comprising administering to the subject an effective amount of DNTs and a chemotherapeutic agent. In one embodiment, the chemotherapeutic agent is a cell cycle inhibitor. In one embodiment, the cell cycle inhibitor is AraC. In one embodiment, the subject has recurrent or relapsing AML, such as recurrent or relapsing AML caused by minimal residual disease (MRD). In one embodiment, the subject has leukemia that is refractory to chemotherapy.

In another embodiment, there is provided a composition comprising DNTs and a chemotherapeutic agent. In one embodiment, the chemotherapeutic agent is a cell cycle inhibitor. In one embodiment, the cell cycle inhibitor is AraC. Optionally, the composition further comprises a pharmaceutically acceptable carrier. In one embodiment there is also provided the use of a composition comprising DNTs and a chemotherapeutic agent for the treatment of cancer. In one embodiment, the composition is for the treatment of AML. In one embodiment, the composition is for the treatment of AML that is resistant to chemotherapy with a chemotherapeutic agent alone.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

One or more embodiments of the disclosure will now be described in relation to the drawings in which:

FIG. 1b shows a representative plot of change in CFSE fluorescence of human CD45+ cells in spleen measured on day 2, 7, 10, and 14 post-injection.

FIGS. 5b and 5c) show that DNTss can mediate in vivo anti-leukemic activity in a dose-dependent manner. NSG mice engrafted with $2.4\times10^6$ blasts #090240, as described above, and were treated with $2\times10^7$ DNTs on day 20 (1×DNT) or on day 10 and day 20 (2×DNT) post blast injection, or remained untreated. On day 34 post blast injection, mice were sacrificed, and the frequency of AML cells engrafted in blast-injected bone marrow (FIG. 5b) and spleen (FIG. 5c) were determined as described above. The average % AML engraftment are shown and the error bar represents SEM (*$p<0.05$, **$p<0.01$)

FIG. 6c) shows a comparison of the percentage specific killing at 4:1 effector to target ratio calculated from the chemotherapy-resistant (n=10) and -susceptible (n=8) samples. The numbers represent average % specific killing value with SEM. n.s.—not statistically significant.

DETAILED DESCRIPTION

Figure 1:
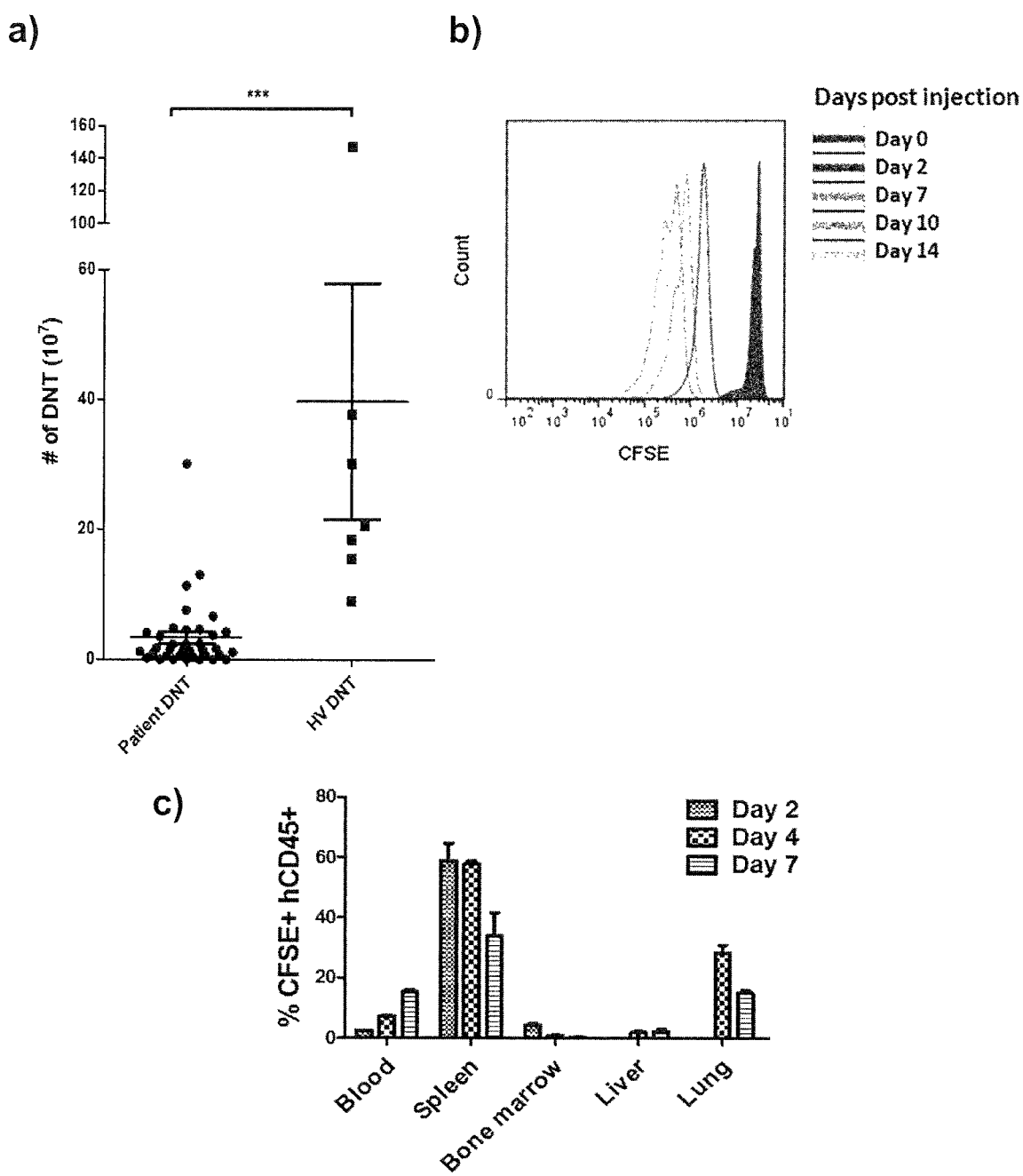
FIG. 1a shows the expansion of DNTs from peripheral blood of AML patients and healthy volunteers and that the DNT's can be expanded ex vivo and in vitro. The number of DNTs expanded from 36 and 7 DNT-expansion cultures from 20 ml PB of 24 patients in remission and 7 HVs were determined, respectively.
FIG. 1b shows the proliferation and FIG. 1c) the migration of ex-vivo expanded HV DNT in a NSG mouse model. $2\times10^7$ CFSE labeled DNTs intravenously injected into NSG mice with $10^5$ IU IL-2 supplement injected intraperitoneally on day 0, 2, 3, and 7.
FIG. 1c shows the frequency and number of human cells harvested from blood, spleen, bone marrow, liver, and lung (n=3). The number the mean value and SEM and error bar represent SEM of each group. (***$p<0.001$).

In one aspect the inventors have determined that DNTs are useful for the treatment of cancer and in particular for the treatment of leukemia or lymphoma. In one embodiment, it has also been determined that DNTs may be used to inhibit the growth or proliferation of cancer cells or to kill cancer cells, including cancer cells that are resistant to chemotherapy. In a preferred embodiment, the DNTs described herein may be used for the treatment AML, or the treatment of recurring or relapsing AML such as AML caused by minimal residual disease. In another embodiment, the DNTs described herein may be used for the treatment of lymphoma.

As used herein, the term "cancer" refers to one of a group of diseases caused by the uncontrolled, abnormal growth of cells that can spread to adjoining tissues or other parts of the body. Cancer cells can form a solid tumor, in which the cancer cells are massed together, or exist as dispersed cells, as in leukemia.

The term "cancer cell" refers a cell characterized by uncontrolled, abnormal growth and the ability to invade another tissue or a cell derived from such a cell. Cancer cells include, for example, a primary cancer cell obtained from a patient with cancer or cell line derived from such a cell. In one embodiment, the cancer cell is a hematological cancer cell such as a leukemic cell or a lymphoma cell. For example, in one embodiment the cancer cell may be a leukemic cell from a subject with AML or a lymphoma cell such as a cell from a subject with Non-Hodgkin Lymphoma (NHL). In one embodiment, the cancer cell may be a leukemic cancer cell in a subject with AML. In one embodiment, the DNTs described herein may be used to inhibit the growth or proliferation of cancer cells in vitro, ex vivo or in vivo. In one embodiment, the DNTs described herein may be used to kill cancer cells in vitro, ex vivo or in vivo.

As used herein, "chemotherapy-resistant cancer" refers to cancers that do not respond to treatment with chemotherapy or that relapses following treatment with chemotherapy. For example, chemo-resistant cells may be primary cancer cells obtained from subjects who do not respond to chemotherapy or cancer cells obtained from subjects who have initially responded to chemo and into remission but experience relapse of the disease. In some subjects, after relapse, the cancer cells no longer respond to chemotherapy and said subjects have chemotherapy-resistant cancer. In one embodiment, chemo-resistant cells are primary leukemic cells directly obtained from subjects.

The term "leukemia" as used herein refers to any disease involving the progressive proliferation of abnormal leukocytes found in hematopoietic tissues, other organs and usually in the blood in increased numbers. "Leukemic cells" refers to leukocytes characterized by an increased abnormal proliferation of such cells.

As used herein, "acute myeloid leukemia" ("AML") refers to a cancer of the myeloid line of blood cells, characterized by the rapid growth of abnormal white blood cells that accumulate in the bone marrow and interfere with the production of normal blood cells.

As used herein, "chronic myeloid leukemia" ("CML") refers to a cancer characterized by the increased and unregulated growth of predominantly myeloid cells in the bone marrow and the accumulation of these cells in the blood.

As used herein, "lymphoma" refers to disease characterized by blood cell tumors that develop from lymphatic cells. Optionally, lymphoma may be Hodgkin Lymphoma (HL) or a non-Hodgkin lymphoma (NHL. Examples of NHL include Burkitt's lymphoma and T cell lymphoma. "Lymphoma cells" refer to lymphocytes characterized by an increased abnormal proliferation of such cells.

The term "subject" as used herein includes all members of the animal kingdom including mammals, and suitably refers to humans. Optionally, the term "subject" includes mammals that have been diagnosed with cancer or are in remission. In one embodiment, the term "subject" refers to a human having, or suspecting of having, a hematological cancer. In one embodiment, the term "subject" refer to a human having AML or suspected of having AML, optionally recurrent or relapsing AML.

In one embodiment, the methods and uses described herein provide for the treatment of cancer. The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease (e.g. maintaining a patient in remission), preventing disease or preventing spread of disease, delay or slowing of disease progression, amelioration or palliation of the disease state, diminishment of the reoccurrence of disease, and remission (whether partial or total), whether detectable or undetectable. "Treating" and "Treatment" can also mean prolonging survival as compared to expected survival if not receiving treatment. "Treating" and "treatment" as used herein also include prophylactic treatment. In one embodiment, treatment methods comprise administering to a subject a therapeutically effective amount of DNTs as described herein and optionally consists of a single administration, or alternatively comprises a series of administrations. In some embodiments, the treatment methods and uses described herein include combination therapy with DNTs and a cell cycle inhibitor.

As used herein, "reducing the growth or proliferation of a cancer cell" refers to a reduction in the number of cells that arise from a cancer cell as a result of cell growth or cell division and includes cell death. The term "cell death" as used herein includes all forms of killing a cell including necrosis and apoptosis.

In one embodiment, the methods and uses described herein involve the administration or use of an effective amount of DNTs and optionally a cell cycle inhibitor. As used herein, the phrase "effective amount" or "therapeutically effective amount" means an amount effective, at dosages and for periods of time necessary to achieve the desired result. For example in the context or treating a cancer such as AML, an effective amount is an amount that for example induces remission, reduces tumor burden, and/or prevents tumor spread or growth of leukemic cells compared to the response obtained without administration of the compound. Effective amounts may vary according to factors such as the disease state, age, sex and weight of the animal. The amount of a given compound that will correspond to such an amount will vary depending upon various factors, such as the given drug or compound, the pharmaceutical formulation, the route of administration, the type of disease or disorder, the identity of the subject or host being treated, and the like, but can nevertheless be routinely determined by one skilled in the art.

In one embodiment, the methods and compositions described herein involve the administration or use of double negative (DN) T cells. DNTs exhibit a number of characteristics that distinguish them from other kinds of T cells. In one embodiment, the DNTs do not express CD4 or CD8. In one embodiment, the DNTs express CD3-TCR complex and do not express CD4 and CD8. In one embodiment, the DNTs have the phenotype CD3+, αβ-TcR+, CD4−, CD8−, CD44−, CD28−. In one embodiment, the DNTs have the phenotype CD3+, αβ-TcR+, CD4−, CD8−, α-Gal−, PD-1−, CTLA4−, CD44+, CD28−. In one embodiment, the DNTs have the phenotype CD3+, CD4−, CD8−, α-Gal−, PD-1−, CTLA4−, CD44+. In one embodiment, the DNTs have the phenotype CD3+, CD4−, CD8−, α-Gal−, Jα24−, Vα14−, CD44+, PD-1−, CTLA4−, CD45R0+. DNTs may be obtained using technologies known in the art such as, but not limited to, fluorescent activated cell sorting (FACS). In one embodiment, DNTs may be isolated from peripheral blood mononuclear cells. Optionally, the DNTs may be autologous cells or allogenic cells.

In one embodiment, the DNTs are autologous cells obtained from a subject with cancer or suspected of having cancer. Optionally, the DNTs are obtained from the subject prior to, during or after chemotherapy. In one embodiment, the DNTs are obtained from a subject prior to, during or after a course of chemotherapy. For example, in one embodiment, the DNTs are obtained after a first round of chemotherapy, or after one or more rounds of chemotherapy.

In some embodiments, the DNTs may be expanded in vitro or ex vivo before use or administration to a subject. Exemplary methods for isolating and expanding DNTs are described in U.S. Pat. No. 6,953,576 "Method of Modulating Tumor Immunity" and PCT Publication No. WO2007/056854 "Method of Expanding Double Negative T Cells", both of which are hereby incorporated by reference in their entirety.

In one embodiment, the DNTs may be obtained from a subject to which the DNTs will later be administered (i.e. autologous cells), in order to treat cancer, reduce the growth or proliferation of cancer cells or kill cancer cells. In one embodiment, the DNTs may be allogenic. As used herein, the term "allogenic" refers to cells which are originally obtained from a subject who is a different individual than the intended recipient of said cells, but who is of the same species as the recipient. Optionally, allogenic cells may be cells from a cell culture. In a preferred embodiment, the DNTs are obtained from a healthy donor. As used herein the terms "healthy volunteer" ("HV") or "healthy donor" ("HD") refer to one or more subjects without cancer. In one embodiment, the healthy donor is a subject with no detectable cancer cells, such as a subject with no detectable leukemic cells.

In one embodiment, the DNTs may be formulated for use or prepared for administration to a subject using pharmaceutically acceptable formulations known in the art. Conventional procedures and ingredients for the selection and preparation of suitable formulations are described, for example, in Remington's Pharmaceutical Sciences (2003—20th edition) and in The United States Pharmacopeia: The National Formulary (USP 24 NF19) published in 1999. The term "pharmaceutically acceptable" means compatible with the treatment of animals, in particular, humans.

In one embodiment, DNTs described herein are surprisingly effective in reducing the proliferation of cancer cells and/or treating cancer in combination with a chemotherapeutic agent. In one embodiment, the chemotherapeutic agent is a cell cycle inhibitor. In one embodiment, the cell cycle inhibitor is a DNA synthesis inhibitor. Accordingly, in one embodiment there is provided a method of treating cancer in a subject comprising administering to the subject DNTs and a chemotherapeutic agent. Also provided is a use of DNTs and a chemotherapeutic agent for the treatment of cancer in a subject in need thereof. In one embodiment, the chemotherapeutic agent is cytarabine (AraC). In one embodiment, the cancer is a leukemia such as acute myeloid leukemia (AML). In some embodiments, DNTs in combination with a chemotherapeutic agent such as a cell cycle inhibitor may be used to treat cancers that are chemotherapy resistant, such as recurring or relapsing AML.

As used herein the term "cell cycle inhibitor" refers to a chemotherapeutic agent that inhibits or prevents the division and/or replication of cells. In one embodiment, the term "cell cycle inhibitor" includes an chemotherapeutic agent selected from Doxorubicin, Melphlan, Roscovitine, Mitomycin C, Hydroxyurea, 5Fluorouracil, Cisplatin, Ara-C, Etoposide, Gemcitabine, Bortezomib, Sunitinib, Sorafenib, Sodium Valproate, HDAC Inhibitors, or Dacarbazine. Examples of HDAC inhibitors include, but are not limited to, FR01228, Trichostatin A, SAHA and PDX101.

As used herein the term "DNA synthesis inhibitor" refers to a chemotherapeutic agent that inhibits or prevents the synthesis of DNA by a cancer cell. Examples of DNA synthesis inhibitors include, but are not limited to, AraC (cytarabine), 6-mercaptopurine, 6-thioguanine, 5-fluorouracil, capecitabine, floxuridine, gemcitabine, decitabine, vidaza, fludarabine, nelarabine, cladribine, clofarabine, pentostatin, thiarabine, troxacitabine, sapacitabine or forodesine. In one embodiment, the DNA synthesis inhibitor is cytarabine or another deoxycytidine analogue as described herein. In one embodiment, the DNA synthesis inhibitor is a DNA elongation terminator and functions in a similar way to cytarabine such as fludarabine, nelarabine, cladribine, or clofarabine.

As used herein, "AraC" (Arabinofuranosyl Cytidine) refers to a compound comprising a cytosine base and an arabinose sugar that is converted into Arabinofuranosylcytosine triphosphate in vivo. AraC is also known as cytarabine or cytosine arabinoside.

In one embodiment, the DNTs and the chemotherapeutic agent are administered to the subject at the same time, optionally as a composition comprising the DNTs and the chemotherapeutic agent, or as two separate doses. In one embodiment, the DNTs and the chemotherapeutic agent are used or administered to the subject at different times. For example, in one embodiment, the DNTs are administered prior to, or after the chemotherapeutic agent. In one embodiment, the DNTs are administered prior to, or after the chemotherapeutic agent separated by a time of at least 1 minute, 2 minutes, 5 minutes, 10 minutes, 30 minutes, 45 minutes, 1 hour, 1.5 hours, 2 hours, 3 hours, 4 hours, 5 hours, 8 hours, 10 hours, 12 hours 16 hours, or 24 hours. Optionally, in some embodiments the DNTs and chemotherapeutic agent are administered to the subject separated by more than 24 hours, 36 hours, 48 hours, 3 days, 4 days, 5 days, 6 days, one week, 10 days, 12 days, two weeks, three weeks, one month, 6 weeks, 2 months, or greater than 2 months. In one embodiment, the DNTs are administered or used between 2 days and 7 days after the chemotherapeutic agent.

In another embodiment, there is provided a composition comprising DNTs and a chemotherapeutic agent. In one embodiment, the chemotherapeutic agent is a DNA synthesis inhibitor. In one embodiment, the DNA synthesis inhibitor is cytarabine or another deoxycytidine analogue as described herein. Optionally, the compositions described herein include a pharmaceutically acceptable carrier such as those described in Remington's Pharmaceutical Sciences (2003—20th edition) and in The United States Pharmacopeia: The National Formulary (USP 24 NF19) published in 1999.

Also provided is the use of a composition comprising DNTs and a chemotherapeutic agent for the treatment of cancer. In one embodiment, the cancer is leukemia, optionally AML. In one embodiment, composition is for use in the treatment of cancer that is resistant to treatment with chemotherapy alone. In one embodiment, the subject has leukemia, optionally AML.

The following non-limiting examples are illustrative of the present disclosure:

EXAMPLE 1

Expansion of DNTs from Peripheral Blood of Healthy Donors 20 ml PB was obtained from HD or AML patients in complete remission after chemotherapy. DNTs were expanded as previously described (Merims et al., 2011). Briefly, CD4+ and CD8+ cells were depleted from peripheral blood mononuclear cells (PBMC) by using RosetteSep™. The remaining CD4− CD8− PBMC were stimulated with plate-bound anti-CD3 antibody for 3 days, washed, followed by re-stimulation with soluble CD3 from day 7 to day 10. Culture media was replaced with IL-2 containing fresh media on day 3, 7 and 10. Cells were counted and stained with anti-CD3, CD4, CD8, iNKT TCR (TCR Vα24-Jα18) antibodies and NKT receptor-antigen (α-Galactosylceramide) at the end of the 2 week expansion. Higher expansion potential of HD DNTs over patient DNTs were demonstrated in expansion cultures prepared with the equal volume of PB of AML patients in complete remission and HD, as significantly higher number of DNTs were obtained when expanded from PB of HD ($3.97 \pm 18.24 \times 10^8$) than that of patient ($3.25 \pm 0.9169 \times 10^7$) (FIG. 1a). Furthermore, DNTs failed to expand in about 50% of AML cases, and higher purity of DNT-population was obtained when PB of HD (90.74%±1.7%) were used compared to 65.0%±19.8% when AML patient PB were used (Table 1). Lower expansion potential and purity of patient DNT may be partly due to exhaustion from encountering of AML cells in patient blood and/or abnormal physiology caused by rigorous chemotherapy. Failure to expand or to acquire pure DNTs for treatment can impose a serious limitation in the use of DNTs in clinical setting. However, these data indicate that such limitations can be avoided using HD DNTs, providing a rationale to focus on allogeneic HD DNTs.

TABLE 1

Frequency of patient and HV DNT cell at the end of expansion. Summary of the purity of DNT cells at the end of expansion cultures set-up with patient or HV peripheral blood.

|  | Patient | HV |
| --- | --- | --- |
| Cultured # | 28 | 24 |
| % CD3 | 94.0 ± 7.2 | 97.04 ± 0.3 |
| Statistics | $P = 0.044$ | |
| % DNT | 65.0 ± 19.8 | 90.74 ± 1.7 |
| Statistics | $P < 0.001$ | |

EXAMPLE 2

Characterizing Human DNTs in a NSG Mouse Model

Successful adoptive T cell therapy relies on the survival and persistence of injected T cells in recipients so these cells can find and eliminate tumor cells. Ideally, the infused T cells are able to further multiply in recipients so that relatively small numbers of T cells will be needed for injection. Since DNTs are generated in a relatively short period (within 2 weeks of initial sample collection), these DNTs are likely early effectors and may proliferate and persist after injection. To test this hypothesis, an immunodeficient NSG mouse model was used. Day 10 ex vivo expanded DNTs were labeled with 5 μM CFSE and $2 \times 10^7$ cells were intravenously injected into sublethally irradiated NSG mice. In order to sustain human DNTs, recipient mice were supplemented with intraperitoneal injection of hrIL-2 (10,000 international unit (i.u.)). Blood, spleen, bone marrow, liver, and lung were harvested on day 2, day 4, and day 7 to determine the proliferation, migration, and the persistence of DNTs in vivo. As shown in FIG. 1b, CFSE dilution was observed from day 2 to day 4, but not from day 4 to day 7, indicating that after adoptive transfer, DNTs proliferated in the first few days post injection. The harvested cells were stained with anti-human CD45 antibody and analyzed using FACS to determine the frequency of DNTs in different tissues over time. Relatively higher frequency of DNTs was detected in blood, spleen, and lung post-injection, while, smaller, but noticeable DNT population was observed in liver and bone marrow up to 7 days post injection (FIG. 1c).

EXAMPLE 3

Development of a Flow-based Killing Assay

Figure 2:
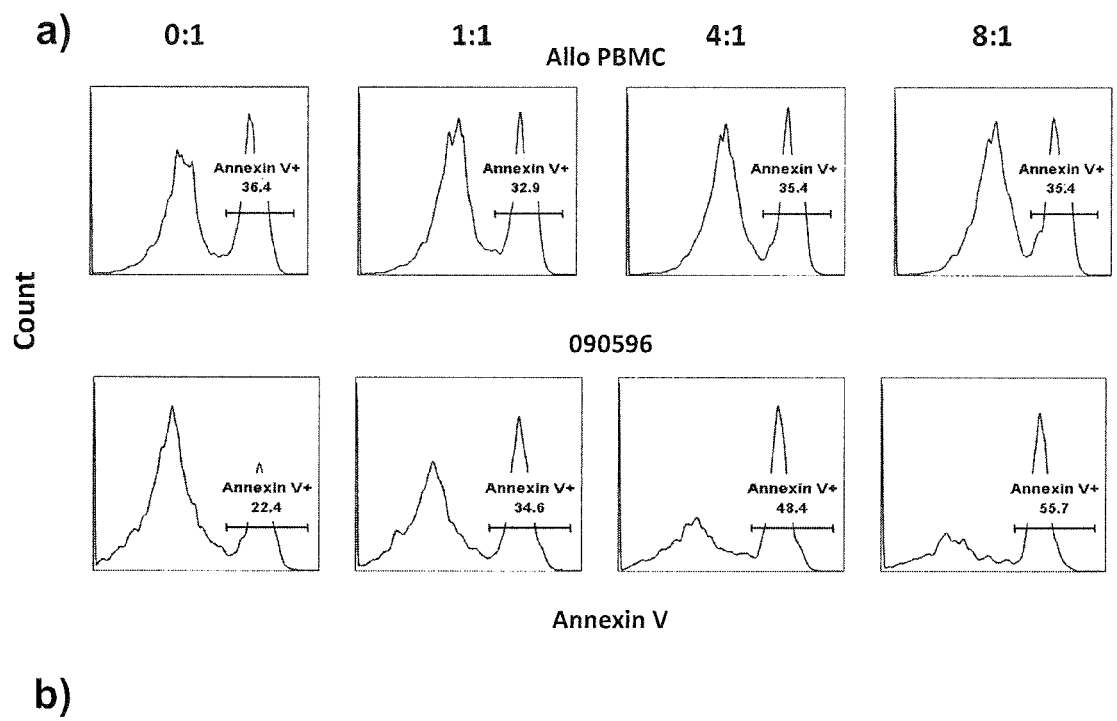
FIG. 2a shows representative plots of a newly developed flow-based killing assay to determine the in vitro susceptibility of primary AML samples to DN T cell mediated cytotoxicity. The assay was conducted with primary AML sample, 090596, and normal PBMC from healthy donor at different effector to target ratios. Annexin V fluorescence was used to determine the level of apoptosis after the co-culture.
FIG. 2b shows results from the flow-based killing assay conducted against healthy and leukemic cells using allogeneic DNTs. Flow-based killing assay conducted with allogeneic DNTs expanded from three healthy donors (HDs) against different targets: AML (filled), AML3 and two primary AML patient blasts, and PBMC and hematopoetic stem and progenitor cells (HSPCs) obtained from three healthy donors (open) to determine the percentage specific killing. Each plot represents the average of three killing assays conducted and the error bars represent SEM.
Figure 2:
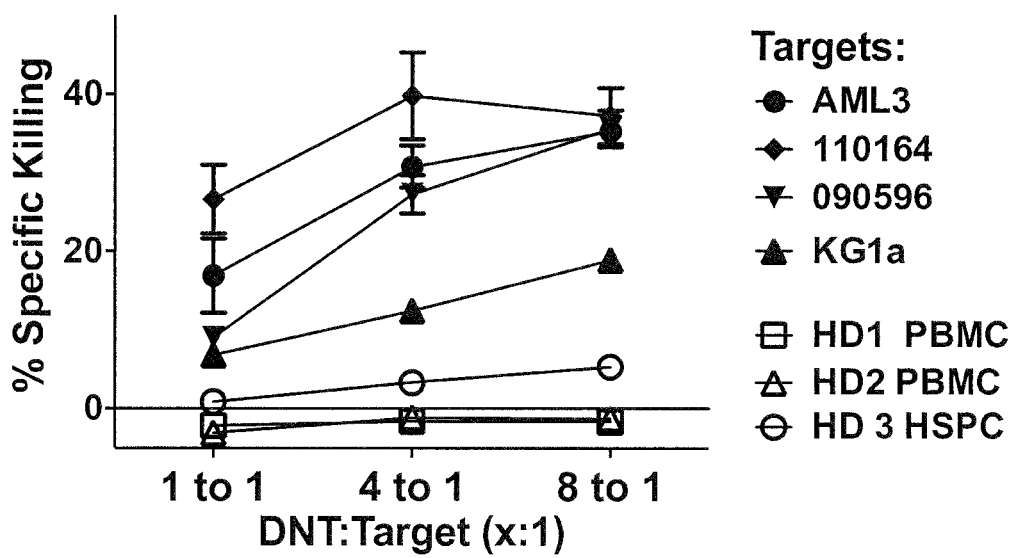

Chromium release assay has been the standard assay that is widely used to determine the level of cytotoxicity of target cells. However, due to a low chromium isotope loading efficiency and high rate spontaneous death of primary AML patient blasts, the widely used chromium-release assay was not optimal for determining the susceptibility of primary AML blasts to DNT-mediated cytotoxicity in vitro. In order to determine the ability of ex vivo expanded DNTs to induce cytotoxic activity against AML in vitro, a new flow cytometry-based killing assay was developed. In this assay, DNTs were labeled with fluorescent membrane dye, PKH-26, and co-cultured with primary AML-blasts for 2 hours at different effector to target ratios. Target and effector cells were cultured alone as controls to determine the level of spontaneous cell death. 2 hour post co-incubation, cells were stained with surface markers CD33 and CD45 antibody to identify AML that is $CD45^{low}$ and/or $CD33^+$, and Annexin V to identify the level of cell-death (FIG. 2). Percentage specific killing was determined as:

% Specific killing=% Annexin $V_{AML-DNT\ co-culture}^+$ − % Annexin $V_{AML\ alone}^+$ Compared to the conventional chromium release assay, the flow-based killing assay is faster, associated with lower background noise, and doesn't require additional preparation of the target cell, such as isotope loading. This new assay allows for directly monitoring the level of AML cell apoptosis mediated by DNTs in a dose-dependent manner, while avoiding the limitations associated with the standard chromium release assay. Furthermore, it can be used to determine the effect of DNTs on different subpopulation of AML population. However, the flow-based killing assay cannot determine the level of the cumulative cell death.

EXAMPLE 4

DNTs Expanded from HD Selectively Target AML in a Dose-dependent Manner but do not Kill Normal Allogeneic PBMC In Vitro To determine the cytotoxicity of allogeneic DNTs towards leukemic cells relative to normal PBMC, the flow-based killing assay was conducted with allogeneic DNTs expanded from 3 different healthy donors against normal PBMCs obtained from two HDs, HSPCs obtained from two HDs, two primary AML patient samples and AML cell lines, OCI-AML3 and KG1a. DNTs from all three donors showed potent killing activity against the two primary AML blasts and AML cell lines in a dose-dependent fashion, but showed no killing activity against allogeneic PBMCs and HSPCs (FIG. 2b). Since DNTs may persist in recipients as seen in Example 2 and FIG. 1c, the co-culture of healthy PBMC and allogeneic DNTs was extended to 14 hrs. Again, DNTs did not induce killing of normal allogeneic PBMC (data not shown). This finding is consistent with the reports in mice that infusion of allogeneic DNTs does not cause pathological lesions in recipients and thus are safe. The ability of DNTs to target allogeneic leukemic cells but not healthy PBMC suggests that allogeneic DNTs are safe to use for treating leukemia patients.

EXAMPLE 5

Figure 3:
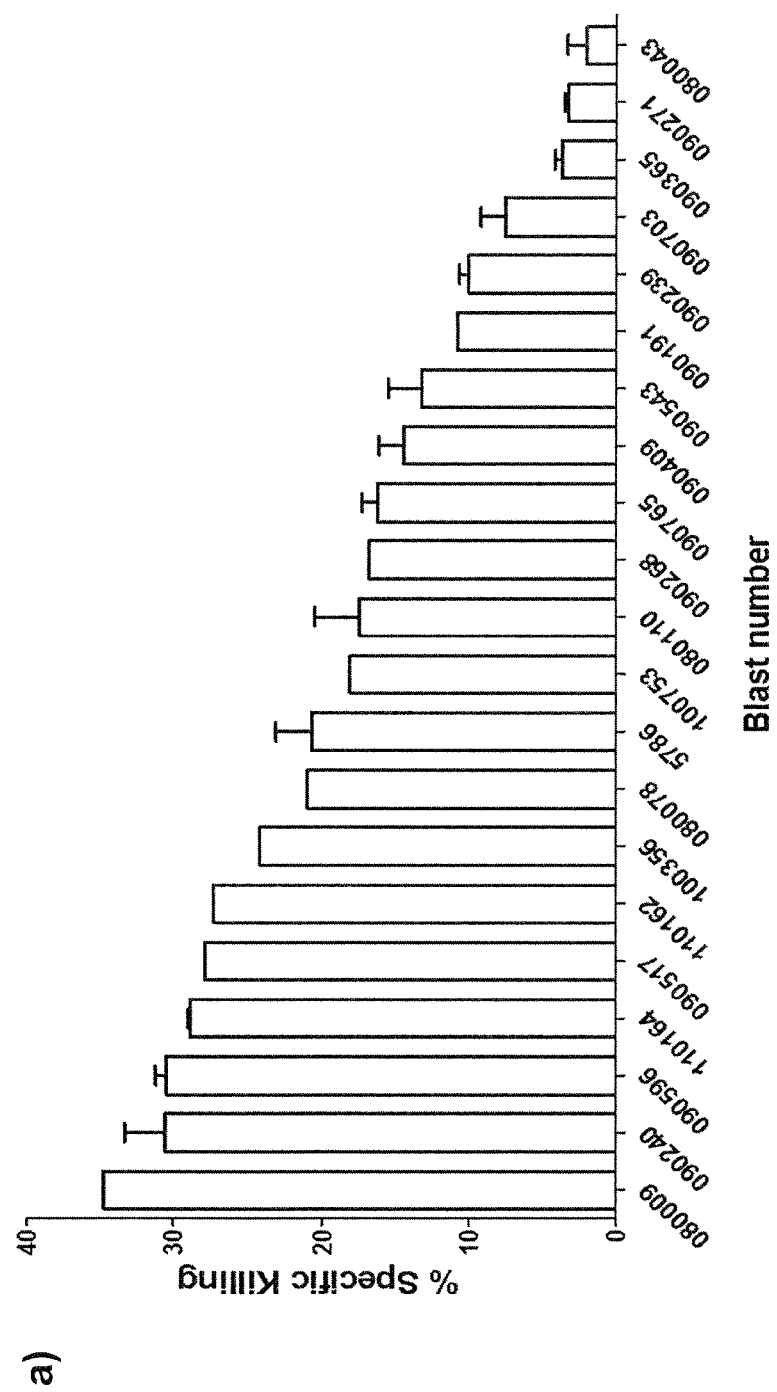
FIG. 3a shows the results of screening patient AML blasts for susceptibility to DN T cell-mediated cytotoxicity in vitro and demonstrates, in one embodiment, that HD DNTs induce potent cytolytic activity against a majority of primary AML blasts in vitro. Percentage specific killing of 21 primary AML samples mediated by allogeneic DNTs at 4:1 effector to target ratio.
FIG. 3b shows that treatment of AML with DNTs prior to injection significantly reduces the level of AML engraftment in vivo. Primary AML blast #0578 was cultured with or without DNTs for 18 hrs and intrafemorally injected into sublethally irradiated (225 cGy) NSG mice (n=5 and n=3, respectively). 31 days post blast-transplantation, mice were sacrificed and the injected bone marrow cells were harvested, stained with human anti-CD45 and anti-CD33, and analyzed by FACS. The level of AML engraftment was determined by the frequency of human CD45+ and CD33+ cells. The average % engraftment is shown for each group and the error bar represents SEM. * shows significant difference compared to blast alone control (*$p<0.05$)
Figure 3:
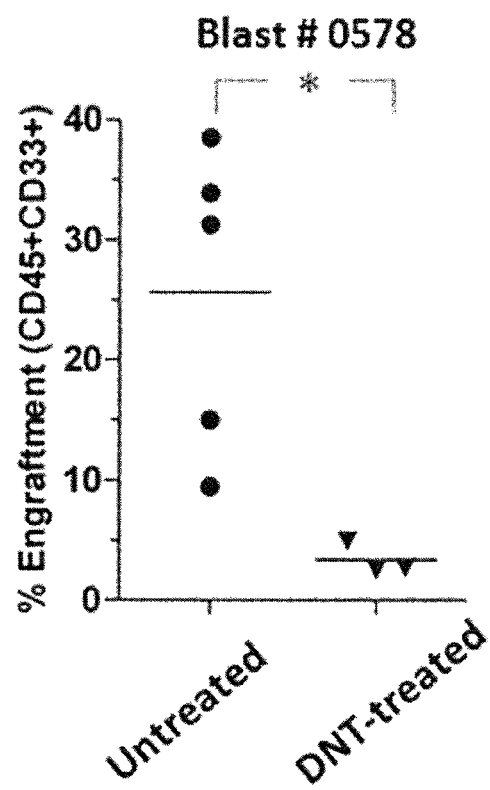

DNTs are Able to Kill Primary AML Blasts In Vitro and Inhibit Leukemia Engraftment in NSG Mice To determine the ability of DNTs expanded from HD to kill leukemic cells, cytotoxicity assays were conducted against primary AML blasts samples obtained from a panel of 23 patients. Although, there was variation in the level of susceptibility, in 19/23 cases, patient primary blasts were susceptible to DNT-mediated cytotoxicity in a dose-dependent manner in vitro, while 4 patient blasts showed high level of resistance (FIG. 3a). These data demonstrate that allogeneic DNTs can effectively target most primary AML blasts.

Although in vitro screening demonstrated significant level of cytotoxicity mediated by DNTs, whether this would translate into lower AML engraftment or transient reduction in AML number remained uncertain. Next, to investigate the effect of DNT on AML engraftment in vivo, the engraftment level of AML treated with or without DNT cells was determined using an established AML-NSG xenograft model (Barabe et al., 2007). Briefly, AML blast #0578 was cultured with or without DNTs for 18 hours, followed by injection into the right femur of sublethally irradiated NSG mice. 31 days post-transplantation, mice were sacrificed, and the engraftment of AML in the injected bone was determined. The AML engraftment level was significantly reduced in mice injected with AML blasts pre-incubated with DNTs compared to no-treatment control, demonstrating that the effect mediated by DNTs can reduce the level of leukemic cells in vivo (FIG. 3b).

EXAMPLE 6

DNTs Mediate Anti-leukemic Activity Against Primary AML in a Dose-dependent Manner In Vivo The reduction in AML engraftment observed in FIG. 3b is likely the result of killing of AML cells in vitro prior to their infusion. To further determine whether infused DNTs can migrate to the site of leukemia engraftment and eliminate preexisting AML in the bone marrow, which more closely resembles conditions in a clinical setting, DNT treatment was administered to NSG mice engrafted with AML blasts, as previously described (Barabe et al., 2007). Briefly, mice were injected with $2.5 \times 10^6$-$5.0 \times 10^6$ primary AML blasts, #5786 or #090392, into the right femur. Ten to fourteen days later at which time the human leukemic cells engrafted the recipients, AML engrafted mice were intravenously injected with either PBS or $2 \times 10^7$ DNTs. Mice were sacrificed after 14-21 days post DNT injection, and cells from the bones injected with AML cells were harvested and stained with fluorescently tagged anti-human CD3, CD33, CD45, CD19, CD34, and CD38 antibodies to determine the level of AML engraftment via FACS analysis. The engraftment frequency of AML cells was compared between DNT- and PBS-treated groups. The frequency of AML blasts #5786 and #090392 were significantly reduced in the injected bone of the DNT treated group compared to PBS treated group (FIGS. 4a and 4b). These results demonstrate that DNTs can migrate from blood to the bone marrow, where AMLs are originated, and target pre-existing AML in bone marrows.

Figure 5:
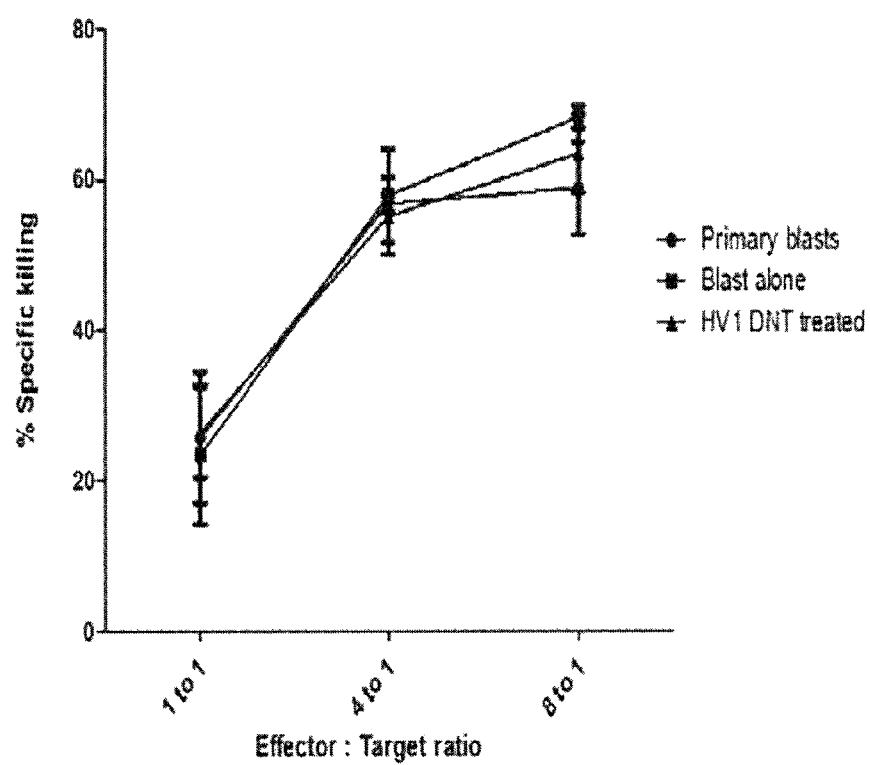
FIG. 5 shows that multiple dose therapy enhances the efficacy of DN T cell therapy. NSG mice engrafted with $2.4\times10^6$ blasts (#090240) were treated with DNTs, or remained untreated 10 days post-blast injection, as described above. 37 days post blast injection, mice were sacrificed and spleen was harvested. AML blasts found in the spleen of DN T cell-treated (▲) or untreated (■) mice, and primary patient AML blast, 090240 (●) were used as targets for the flow-based killing assay conducted with DNTs expanded from 2 healthy donors, and the % specific killing for each target was determined, as described in Example 3. To determine if the residual AML blasts after DNT treatment were resistant to DN T cell-mediated cytotoxicity, the residual blasts were isolated from spleens of DN T cell- and PBS-treated mice. The susceptibility of harvested residual AML cells and the primary AML blast initially used for engraftment to DN T cell-mediated cytolysis in vitro was determined using flow-based killing assay (FIG. 5a). Based on this observation, the efficacy of multi-dose DN T cell treatment was tested.
Figure 5:
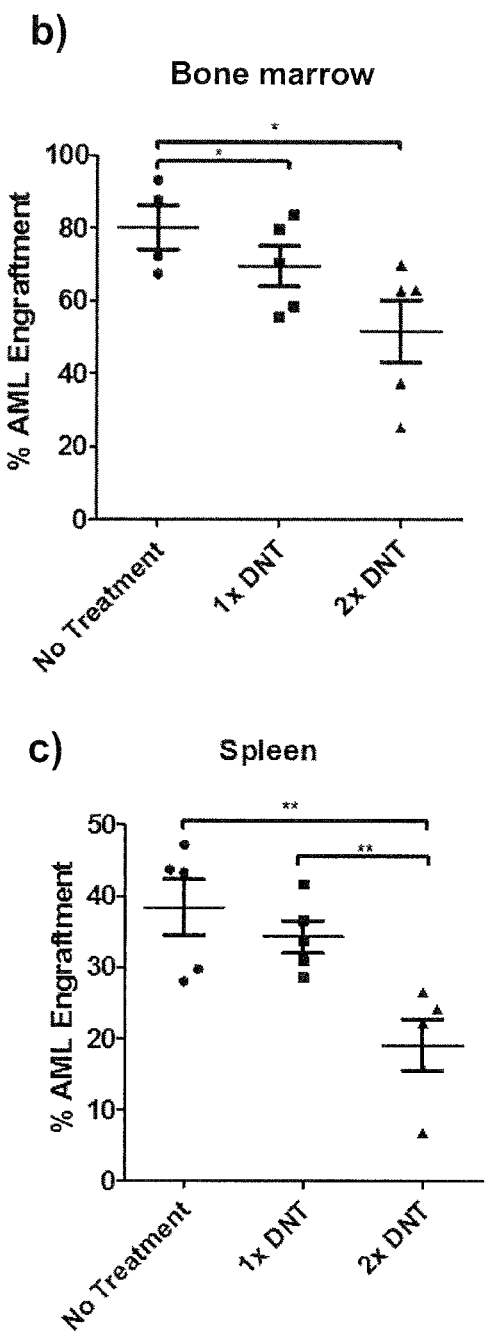

While DNT treatment significantly reduced the frequency of AML engraftment, some residual blasts in DNT treated group were observed. Two possibilities may account for the residual AML cells: 1) these cells are resistant to DNT-mediated cytotoxicity: 2) one dose DNT treatment may not be sufficient to eliminate a large numbers of preexisting AML cells. To determine whether the remaining AML cells are susceptible to DNT-mediated cytotoxicity, residual AML blasts were isolated from DNT-treated and untreated group and used as targets along with primary AML blast initially used for the engraftment in our flow-based killing assays. The residual AML blasts obtained from DNT-treated mice were equally susceptible to DNT-mediated killing in vitro as primary AML cells and AML cells obtained from PBS treated group (FIG. 5a), indicating that it was unlikely that persistence of AML cells is due to their resistance to DNT killing. In addition, we observed that the ability of DNTs to reduce AML engraftment inversely correlated with the frequencies of preexisting AML cells in recipients (FIG. 5b), supporting the notion that more than one DNT treatment may further reduce the level of AML engraftment. To test this hypothesis, NSG mice were injected intrafemorally with high engraftment blast #090240. Ten days after AML cell injection, the recipient mice were intravenously infused with one dose DNTs as before. After another 10 days, half of the DNT-treated mice were treated with a second dose of DNTs from the same donor. Control mice were injected with PBS as controls. The group treated with two doses of DNTs showed the lowest level of AML engraftment in bone marrows and in spleen (FIGS. 5b and 5c). In spleen, second dose DNTs significantly reduced the frequency of the blast compared to group treated with single dose of DNTs (FIG. 5c). Though statistically not significant, the same trend was observed for the bone marrows (FIG. 5b), perhaps due to a very high frequency of preexisting AML cells in the bone marrow. Taken together, these data indicate that DNTs are able to eliminate AML cells and inhibit leukemia engraftment in xenograft models. It is therefore likely that multiple injections can enhance the efficacy of DNT treatment. Furthermore, DNT may be particularly effective as an adjuvant therapy after elimination of the majority of AML cells by conventional chemotherapy for targeting MRD. The initial administration or use of chemotherapy such as AraC may help eradicate the majority of cancer cells, followed by a dose of DNTs may be more effective against relatively fewer cells that remain that are chemotherapy resistant.

EXAMPLE 7

Chemotherapy Resistant AML is Susceptible to DNTs

Chemotherapy is the standard treatment used for AML patients. Chemotherapy is effective at reducing the leukemia load and achieving the initial remission of the disease. However, it often fails to achieve complete clearance of the disease leading to a high rate of relapse in AML patients.

One of the major limitations of AML patient treatment is therefore the failure to effectively target chemotherapy resistant AML, which results in the high rate of relapsing AML. To study whether DNTs can target chemotherapy resistant AML, AML samples obtained from chemotherapy susceptible and resistant patients were used as targets for DNTs in our in vitro killing assays. Remarkably, 7 out of 10 chemotherapy resistant (FIG. 6a) and 7 out of 8 chemotherapy susceptible (FIG. 6b) AML patient samples showed significant susceptibility to DNTs. Furthermore, the level of average specific killing was comparable in the chemotherapy-susceptible and—resistant groups, 19.8±3.7% and 16.6±4.1, respectively (FIG. 6c). The killing of chemotherapy resistant AML by DNTs was further validated by in vivo experiments conducted with samples obtained from chemotherapy resistant, non-responding (#5786, FIG. 4a) and relapsing (#090240, FIGS. 5b and 5c), patients, as described in Example 6. DNT treatment significantly reduced the AML load in both samples. These results demonstrate that DNTs can be used as potential immunotherapy to treat chemotherapy non-responding patients and highlight the potential for clinical use of DNTs against chemotherapy-resistant MRD to achieve relapse-free remission.

EXAMPLE 8

Potential LSC-targeting Activity Mediated by DNTs

Figure 7:
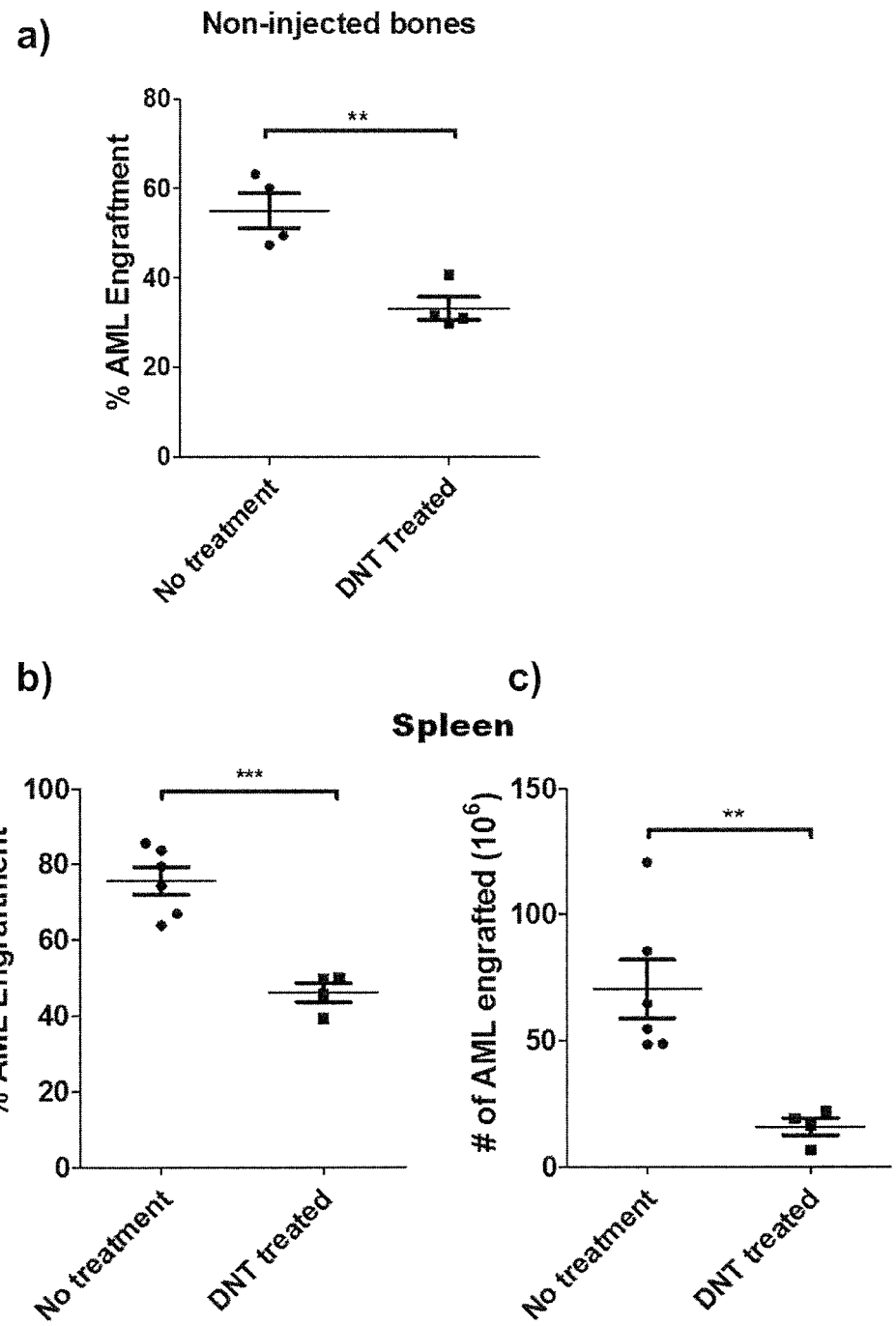
FIG. 7 shows the potential targeting of LSC mediated by DNTs in vivo. NSG mice engrafted with highly aggressive blast, 090240, were treated with $2\times10^7$ DNT or PBS 10 days post blast injection. On 39 days post blast injection, mice were sacrificed, and the frequency or the frequency and the number of AML cells in non-injected tissues, non-injected bones (FIG. 7a) and spleen (FIGS. 7b and 7c) were determined, respectively. Each line represents the average and the error bar represents SEM. (*$p<0.05$, $p<0.01$, *$p<0.001$)

Previously, the potential cytotoxic activity of DNTs against LSCs was demonstrated as DNTs targeted AML with expression of CD34, a marker expressed by LSC (Merims et al., 2011). However, as not all CD34+ cells represent the LSC population, the effect of DNTs on LSC remained uncertain. In vivo experiments done with highly aggressive AML sample, #090240 showed high level of AML engrafted in non-injected tissues, spleen and non-injected bones. Due to their cancer-initiating and populating characteristics, engraftment of AML in non-injected tissues is thought to be mediated by LSCs. The results provided herein provide evidence of the potential killing of LSCs mediated by DNTs as DNT treatment reduced the level AML engraftment in non-injected bones (FIG. 7a) and spleen (FIGS. 7b and 7c). Whether this reduction is caused by the killing of non-LSC AML at the site of engraftment or killing of engraftment-inducing LSC is unknown.

EXAMPLE 9

Efficacy of DNT- and Chemo-combination Therapy

Figure 8:
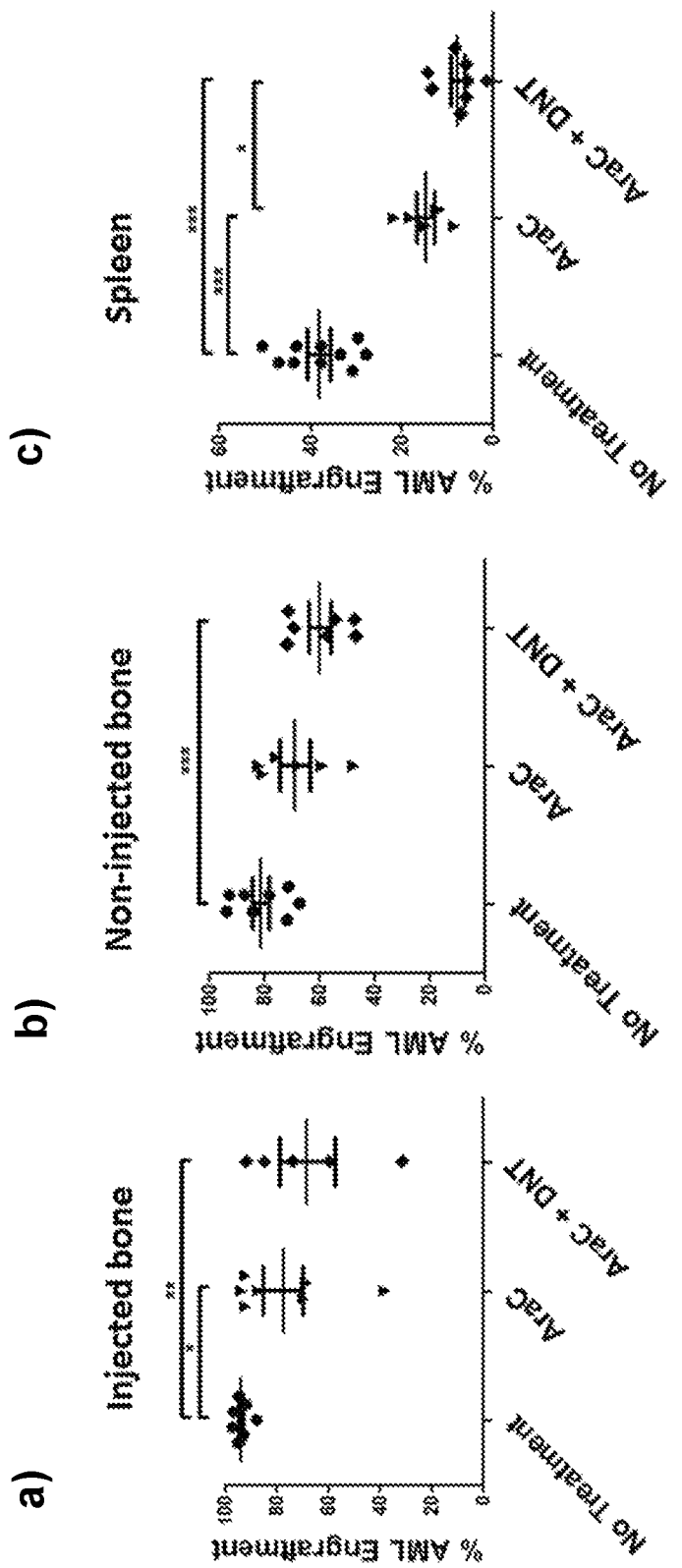
FIG. 8 shows the anti-leukemic activity of DNT- and chemo-combination therapy. NSG mice engrafted with blast, 090240, were treated with PBS (no treatment, ●), or AraC (AraC, ■), or AraC followed by DNTss (AraC+DNT, ♦). On 37 days post blast injection, mice were sacrificed, and the frequency of AML cells in injected bone (FIG. 8a), non-injected bones (FIG. 8b) and spleen (FIG. 8c) were determined. Each line represents the average and the error bar represents SEM (*$p<0.05$, $p<0.01$, *$p<0.001$).

Chemotherapy is effective at reducing the size of leukemia in large-number and achieving the initial remission of the disease. However, it is not very effective at achieving the complete clearance of the disease, and thus comes with the limitation of MRD mediated relapsing AML. In contrast, DNT therapy is effective at specifically targeting AML, including cancers that cannot be killed by chemotherapy, as shown in Example 7. However, the level of AML-load seems to be an important determining factor for the efficacy of DNT therapy, as is in other cellular therapies against other cancers. To determine if DNT- and chemo-therapy can be used in combination to overcome the limitations associated with individual therapy, #090240-AML engrafted NSG mice were intraperitoneally injected with standard chemo-drug, arabinofuranosyl cytidine (AraC), at 60 mg/kg over five days, starting on 13 days post blast injection. 3 days after the last Ara-C injection, mice were injected with DNT or PBS with IL-2 supplement, as previously described. 14 days post DNT injection, mice were sacrificed, and bone marrows and spleen were harvested. There was a significant reduction in the frequency of AML with the combination therapy in injected bone (FIG. 8a), non-injected bone (FIG. 8b) and spleen (FIG. 8c). Although statistically not significant, combination therapy also resulted in lower average AML engraftment frequency than either of the treatments alone in all three tissues. In spleen, the group that received the combination therapy had significantly lower level of AML engraftment than the group that received AraC therapy alone (FIG. 8c). These data collectively demonstrate the additive anti-leukemic effect mediated by DNT- and chemo-therapy, and the potential of utilizing DNT therapy after chemotherapy to target residual blasts post-chemotherapy in clinic. Combination therapy with DNT and chemotherapeutic agents such as AraC is therefore likely to be more effective in treating AML than either immunotherapy with DNT or chemotherapy alone. Previously, it was not known whether chemotherapy followed by DNT would result in any advantage in the reduction of cancer cells. As set out above, AraC and DNT appear to target different AML cells and combination therapy may therefore result in a significant advantage compared to either treatment alone.

Figure 9:
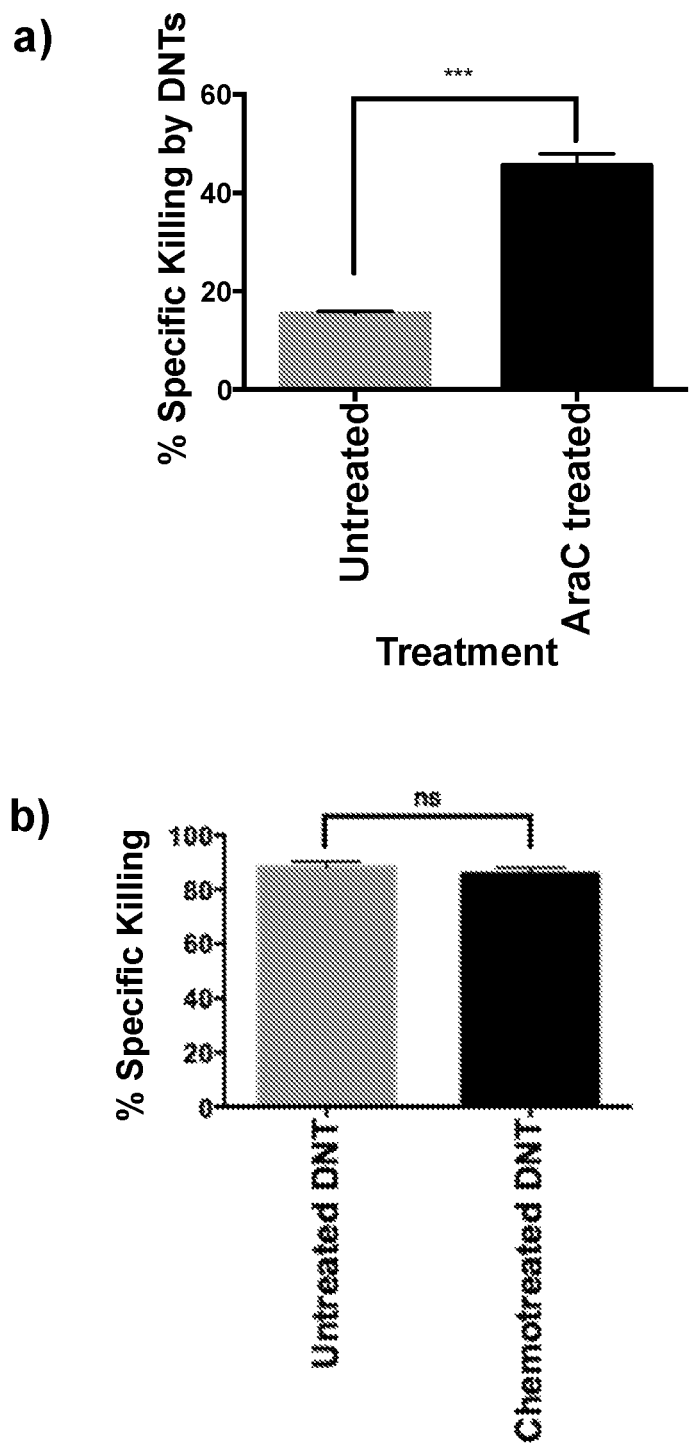
FIG. 9a shows the effect of a chemotherapy drug, AraC on the susceptibility of AML cells to the cytotoxic activity of DNTs. KG1a was treated with 1 ug/ml AraC or PBS for 14 hrs. Subsequently, KG1a were co-cultured with ex vivo expanded DNTs from healthy donors at 4:1 effector to target ratio for 4 hours. The level of specific killing induced for each targets was determined as described above.
FIG. 9b shows that Ara-C does not interfere with the cytotoxic function of DNTs. Ex vivo expanded DNTs were pre-treated with Ara-C or PBS for 14 hours, and was used for in vitro killing assay against AML cell line, OCI-AML3 at 4:1 effector to target ratio for 4 hours. The level of specific killing induced by each DNTs were determined as described above.

To determine whether the superior anti-leukemic activity of AraC and DNT combined treatment is due to synergistic effect of the two or merely an additive effect of two different treatments, in vitro killing assay was conducted against leukemic stem cell-like AML cell line, KG1a. KG1a treated with AraC or PBS for 14 hours were co-incubated with DNTs. AraC rendered KG1a significantly more susceptible to DNTs as % killing induced by DNTs was 15.38±0.51% against untreated KG1a and 45.59±2.34% for AraC-treated KG1a (FIG. 9a). Nevertheless, treating DNT cells with AraC for 14 hrs prior to in vitro killing assay against OCI-AML3 had no effect on DNT mediated cytotoxicity, suggesting that DNTs can be used simultaneously with chemotherapy drugs (FIG. 9b).

EXAMPLE 10

Selective Cytotoxic Activity of Allogeneic Double Negative T Cells Against Acute Myeloid Leukemia As set out below, the inventors have determined that allogeneic human DNTs have potent anti-leukemic effect against primary AML patient blasts, including chemotherapy-resistant ones in vitro and in xenograft models without detectable toxicity to normal cells and tissues. These findings support the use of DNTs expanded from HDs as a new cell therapy for AML patients to overcome the limitations of current treatments and increase patient survival.

Ex Vivo Expanded Allogeneic DNTs Induce Potent Cytolytic Activity Against Primary AML Patient Blasts In Vitro and In Vivo.

Previously, the cytotoxicity of ex vivo expanded DNTs from peripheral blood (PB) of AML patients in complete remission against autologous CD34$^+$ leukemic blasts was demonstrated in vitro (Merims et al., 2011), but only 30% of patients' DNTs could be expanded (12 out of 36 cultures expanded to 3×10$^7$ DNTs or higher).

Figure 10:
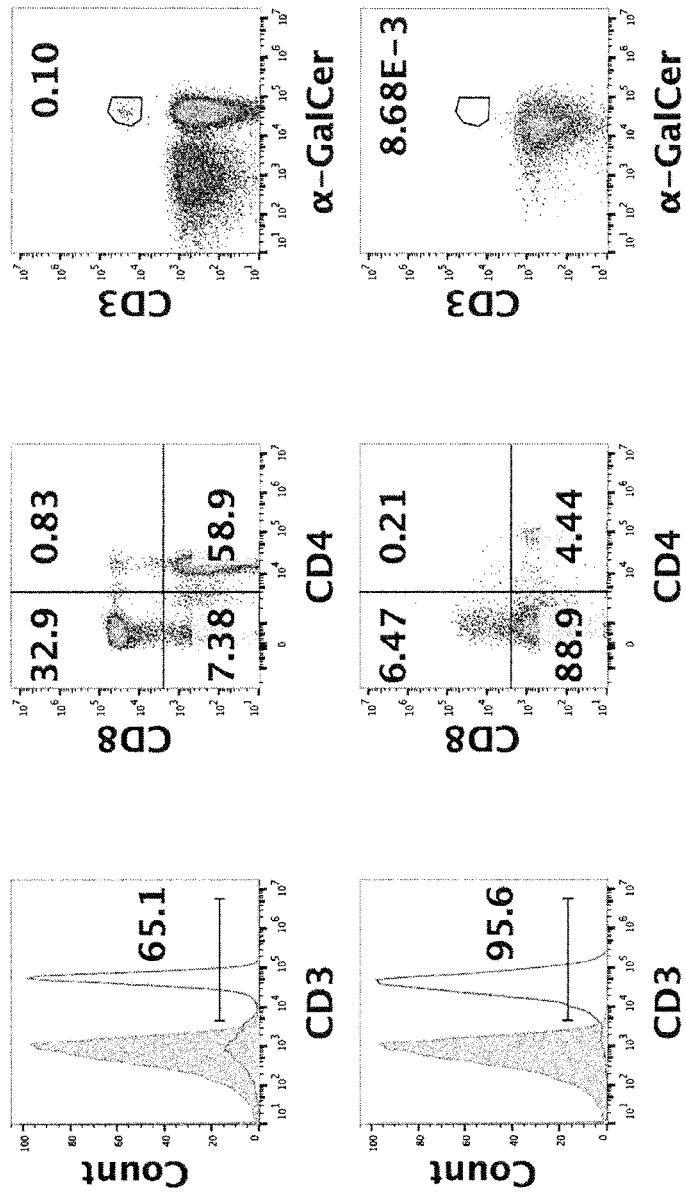
FIG. 10 shows the phenotypic characterization of PBMCs and DNTs post-expansion. PBMCs (top panels) or DNTs harvested 14 days after expansion (bottom panels) were stained with antibodies against human CD3, CD4, CD8, and αGalCer-CD1d. Filled histograms represent the fluorescence minus one (FMO) control. Numbers on the graphs represent the frequency of the population in each quadrant or gate. (***$p<0.001$)

Here, the inventors have surprisingly shown that DNTs can be expanded from all HDs tested with an average of 10-fold higher total number of DNTs than that of AML patients (FIG. 1a) and significantly higher purity (90.74%±1.7% for HD DNTs vs. 65.0%±19.8% for patient DNTs) (FIG. 10).

Infusion of DNTs does not Attack Normal Allogeneic PBMC and CD34$^+$ HSPC.

Figure 11:
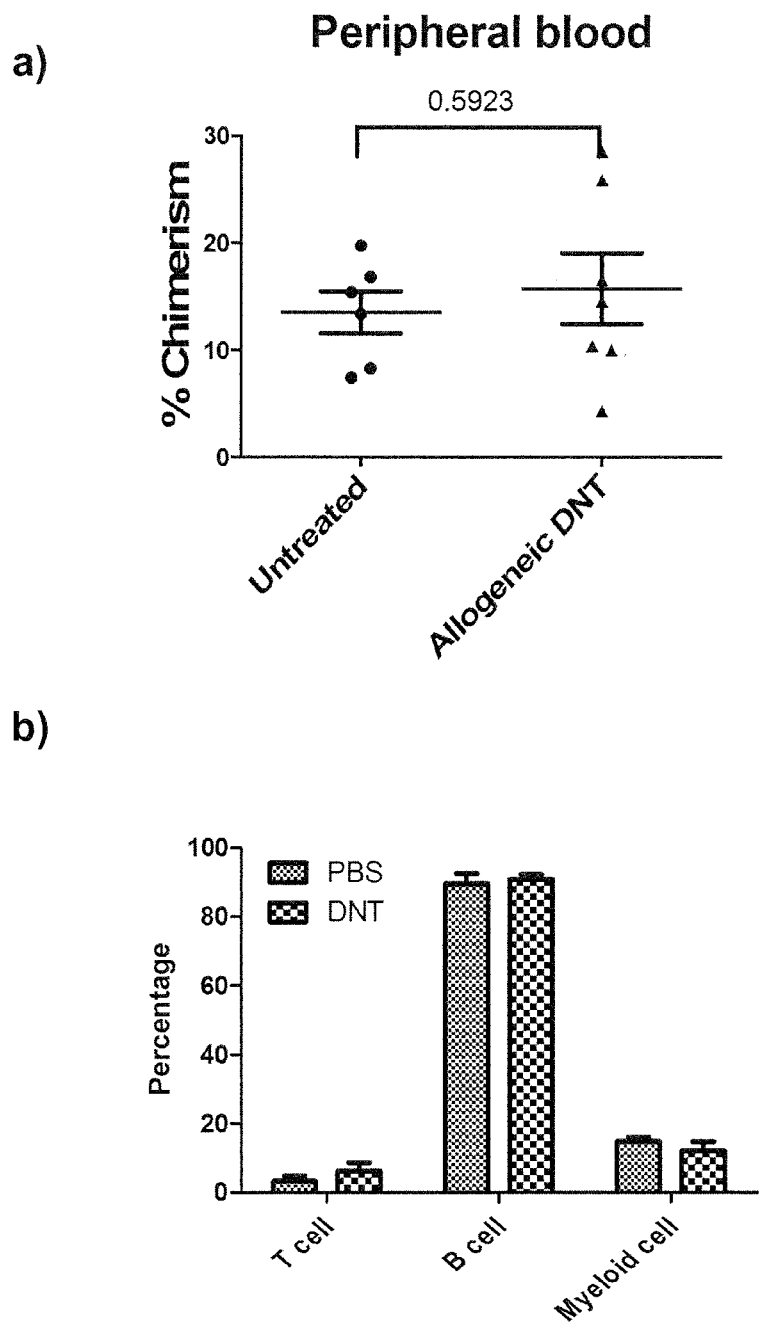
FIGS. 11a and 11b show that DNTs from healthy donors (HD) do not attack hematopoietic stem cells in vivo and affect their differentiation. $CD133^+CD34^+$ human HSPC were intravenously injected into sublethally irradiated NSG mice ($5\times10^6$ cells/mouse, n=13). Eight weeks post HSPC injection, 7 mice were intravenously injected with $10^7$ ex vivo expanded allogeneic DNTs. Eight weeks post DNT injection, cells from PB were harvested and stained with anti-mouse CD45, anti-human CD45, CD3, CD19, CD11b, CD56, CD33, and CD34 antibodies. The percentage of human leukocytes (FIG. 11a) and its subsets (FIG. 11b) were determined by flow cytometry analysis. Horizontal bars represent the mean value and the error bars represents SEM of each group.

To further determine the potential effect of allogeneic DNTs on normal HSPC engraftment and differentiation, NSG mice were humanized by engraftment of CD34$^+$ CD133$^+$ HD HSPC and treated with DNTs from different HDs. As reported by others (McDermott et al., 2010, Drake et al., 2011), consistently high chimerism (~70-80%) was observed within the spleens and BM, of engrafted mice, while chimerism in peripheral blood was ~15%. Importantly, no difference was observed in the frequency (FIG. 11a) and differentiation of lineages (FIG. 11b) between DNT-treated and non-treated mice. These findings suggest that DNTs do not target HSPC nor interfere with the differentiation of HSPC into hematopoietic lineages. Together, these results support the safety of DNTs as a new cancer immunotherapy by demonstrating that ex vivo expanded allogeneic DNTs have potent anti-leukemia activities, yet are not cytotoxic to normal tissues and hematopoietic cells.

Allogeneic DNTs Prolong the Survival of NSG Mice with Lethal AML.

Figure 12:
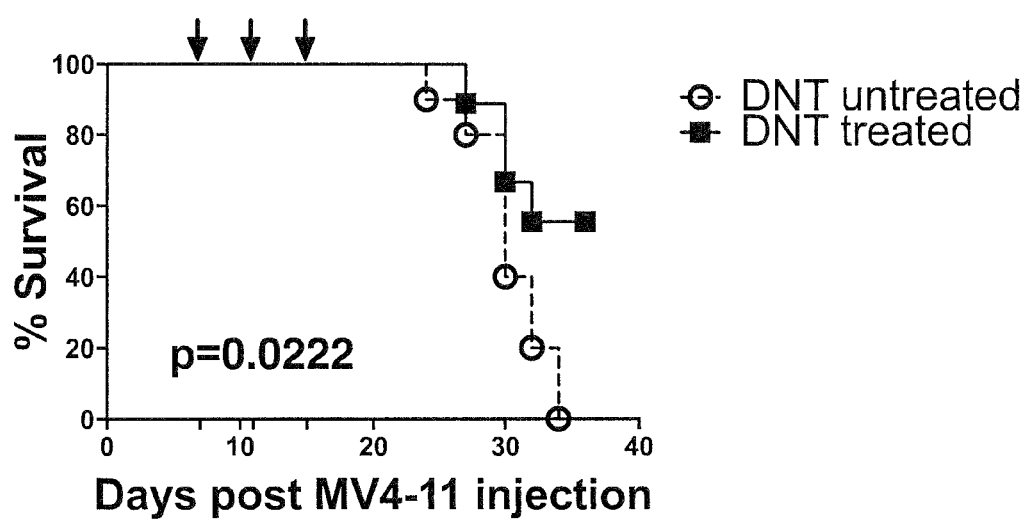
FIG. 12 shows that DNT cells can rescue NSG mice injected with lethal dose of AML cell line. Sublethally irradiated NSG mice were injected with $10^6$ MV4-11 intravenously, and starting on day 7, received three injections of $2\times10^7$ DNT (n=9) or PBS (n=10) with four days apart between injections. Arrows represent the time of DNT or PBS injections. $p<0.01$; *$p<0.001$.

In contrast to the majority of primary AML blasts, AML cell line, MV4-11 is lethal to NSG mice. When three injections of DNTs were given to MV4-11 injected NSG mice, significant survival benefit was observed in DNT-treated group (FIG. 12). Collectively, these results demonstrate that ex vivo expanded allogeneic DNTs are cytotoxic to chemotherapy resistant primary AML blasts in vitro and effective in reducing leukemia loads in xenograft models.

Discussion

Figure 4:
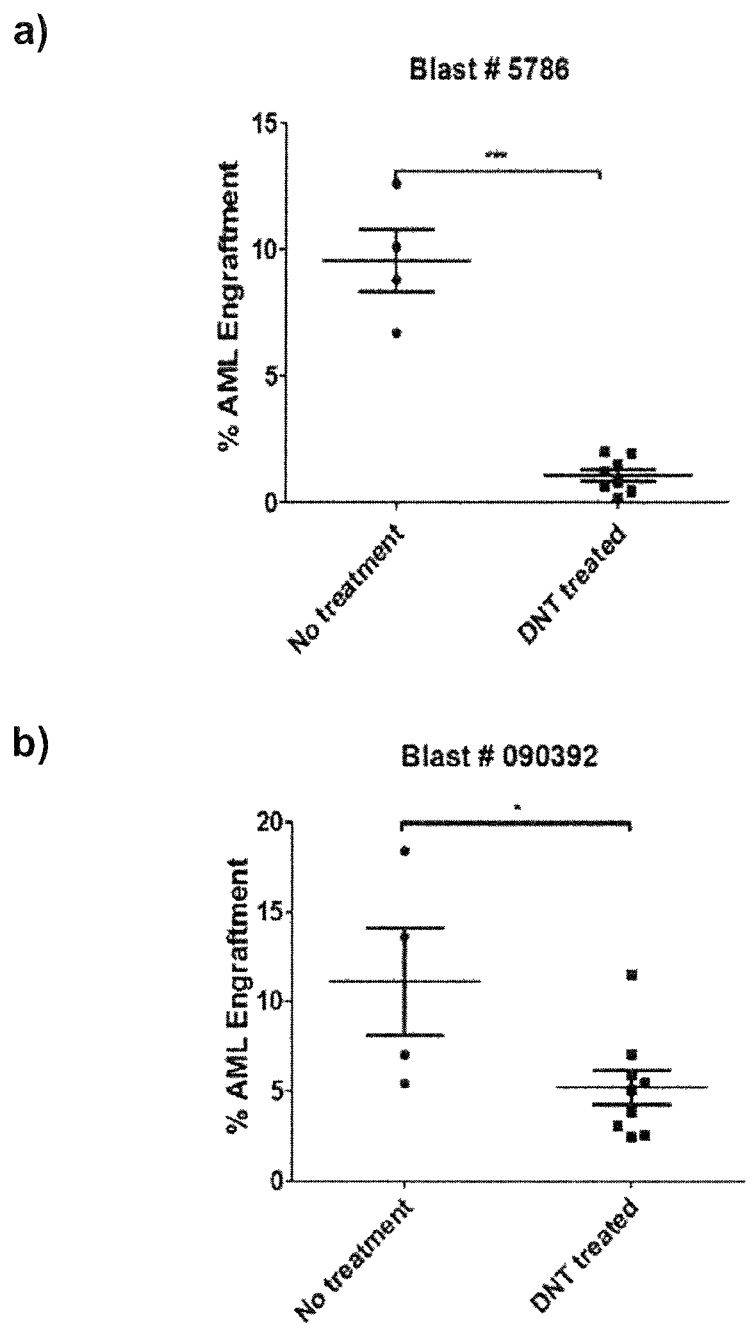
FIG. 4 shows that anti-leukemic activity is mediated by allogeneic DNTs and that allogenic DNTs can target primary AML blasts in vivo. Sublethally irradiated NSG mice were engrafted with primary AML by intrafemoral injection of $5.0\times10^6$ #5786 (FIG. 4a) or #090392 (FIG. 4b) patient blasts. 10 or 14 days post #5786 or #090392 injection, respectively, the mice were injected i.v. with $2\times10^7$ HV DNTs or PBS. On day 14-21 post DNT injection, mice were sacrificed, and cells from blast-injected bones were stained with anti-human CD38, CD33, CD34, and CD45 fluorescently-tagged antibodies. The frequency of AML cells in the blast-injected bones was determined by the percentage of human CD38, CD33, CD33 and/or CD45 positive cells.
Figure 6:
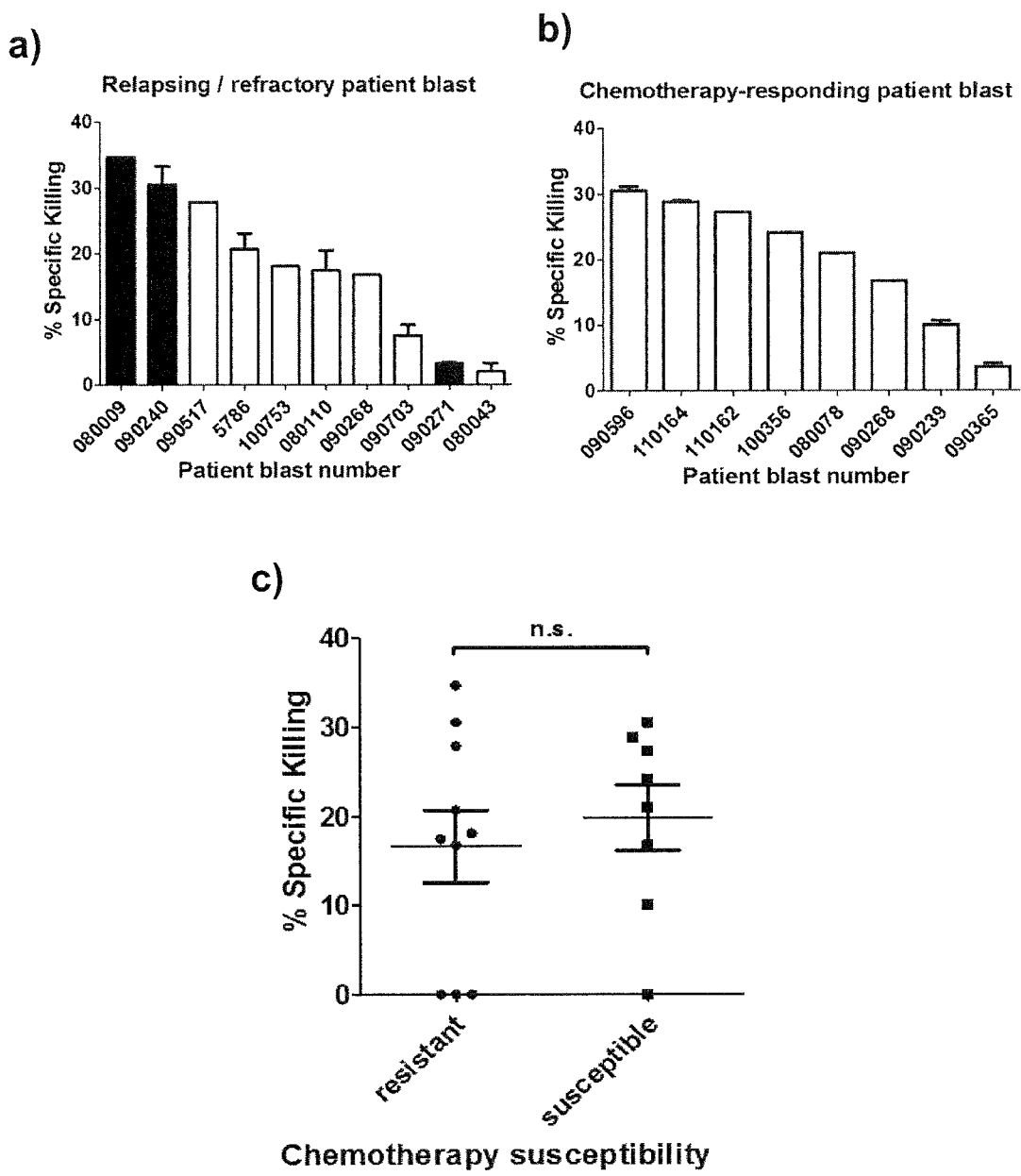
FIG. 6 shows that DNTs can target both chemotherapy-susceptible and chemotherapy-resistant AML. Flow-based killing assay was conducted against primary AML samples obtained from chemotherapy-resistant, refractory (empty) or relapsing (filled) patients (FIG. 6a) or chemotherapy-susceptible patients (FIG. 6b). Cells were co-incubated at 4:1 effector to target ratio for 2 hours.

Despite the extensive use of chemotherapy to treat AML patients for the past decade, the high rate of relapse due to chemotherapy resistance remains a major challenge to patient survival (Lin & Levy, 2012, Hourigan & Karp, 2013). Allogeneic-HSCT is a potential curative treatment for AML patients, but its application is limited by associated toxicity and donor availability (Brissot & Mohty, 2015, Vyas et al., 2015, MacDonald et al., 2013). As evident in HSCT, T cell and NK cell therapy, the graft-versus-leukemia effects in allogeneic settings are stronger than those in autologous settings due to donor immune cells recognizing allo-antigens, which elicit robust immune reactions toward transformed cells (Arpinati & Curti, 2014, Campbell & Hasegawa, 2013, Ruggeri et al., 2002, June, 2007). Allogeneic DNTs from healthy individuals can effectively target a large array of primary AML blasts in vitro (FIGS. 2b, 3a, 6a and 6b) and in vivo (FIGS. 4 and 6c). Further, residual blasts post-DNT treatment showed a high level of susceptibility to DNT killing, one which was comparable to that associated with the untreated group and primary blast initially used for engraftment (FIG. 5a) This suggests that unlike chemotherapy, AML blasts do not develop resistance to DNTs after the treatment. Consistent with this, multiple DNT treatments further reduce the leukemic burden (FIGS. 5b and 5c). More importantly, DNTs effectively targeted chemotherapy resistant AML cells (FIGS. 5b, 5c, and 6). These data suggest that DNTs target AML cells via mechanisms that differ from chemotherapy and that DNTs may be used either alone for chemotherapy non-responding AML or in combination with chemotherapy to target relapse-initiating chemotherapy resistant AML to overcome the current limitation in AML patient treatment.

In agreement with the lack of allogeneic response (FIGS. 2b and 12), DNTs from a single donor could kill array of primary AML cells and AML blasts from single patient were lysed to a similar degree by DNTs from different donors (data not shown). These features point to a broader applicability of DNTs as a cellular therapy and avoid the need for producing therapeutic cells from each patient. Furthermore, with a recent success in treating lymphoma (Maude et al., 2014), studies utilizing CAR technology to target AML has become more active (Kenderian et al., 2015, Lichtenegger et al., 2015, Tettamanti et al., 2014, Wang et al., 2015). Given their readily expandability and constitutively high expression of effector molecules with anti-cancer immune responses (Merims et al., 2011), DNTs may serve as a good cellular vector for CAR technology to further enhance their anti-tumor activity. Further, as primary blasts obtained from chemotherapy resistant and relapsing patients are susceptible to DNT-mediated cytotoxicity in vitro and in vivo (FIGS. 6 and 7), DNTs may be used as the first line to treat chemotherapy refractory patients or as a consolidation therapy after the conventional chemotherapy to target chemotherapy-resistant minimal residual diseases.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

Menzin J, Lang K, Earle C C, Kerney D, Mallick R. The outcomes and costs of acute myeloid leukemia among the elderly. Arch Intern Med. 2002; 162:1597-1603.

Ungewickell A, Medeiros B C. Novel agents in acute myeloid leukemia. Int J Hematol. 2012; 96:178-185.

Hoang V T, Zepeda-Moreno A, Ho A D. Identification of leukemia stem cells in acute myeloid leukemia and their clinical relevance. Biotechnol J. 2012; 7:779-788.

Bucisano F, Maurillo L, Del Principe M I, Del Poeta G, Sconocchia G, Lo-Coco F, Arcese W, Amadori, S, Venditti A. Prognostic and therapeutic implication of minimal residual disease detection in acute myeloid leukemia. Blood. 2012; 119:332-341.

Ferrara F, Palmieri S, Mele G: Prognostic factors and therapeutic options for relapsed or refractory acute myeloid leukemia. Haematologica 89 (8): 998-1008, 2004.

Garces-Eisele J. Molecular biology strategies to detect residual disease. Hematology. 2012; 17 Suppl 1:S66-8.

Lin T L, Levy M Y. Acute myeloid leukemia: focus on novel therapeutic strategies. Clin Med Insights Oncol. 2012; 6:205-217.

Ishizawa K, Rasheed Z A, Karisch R et al. Tumor-initiating cells are rare in many human tumors. Cell Stem Cell. 2010; 7:279-282.

Kadowaki N, Kitawaki T. Recent advance in antigen-specific immunotherapy for acute myeloid leukemia. Clin Dev Immunol. 2011; 2011:104926.

Vaz A P, Ponnusamy M P, Batra S K. Cancer stem cells and therapeutic targets: an emerging field for cancer treatment. Drug Deliv Transl Res. 2013: 3(2):113-120.

Alatrash G Molldrem J J. Immunotherapy of AML. Cancer treatment and research. 2009: 145:237-55

Shlomchik W D. Graft-versus-host disease. Nat Rev Immunol. 2007; 7:340-352.

Rosenberg S A, Packard B S, Aebersold P M et al. Use of tumor-infiltrating lymphocytes and interleukin-2 in the immunotherapy of patients with metastatic melanoma. A preliminary report. N Engl J Med. 1988; 319:1676-1680.

Teague R M, Kline J. Immune evasion in acute myeloid leukemia: current concepts and future directions. J Immunother Cancer. 2013;1(13)

Kochenderfer J N, Yu Z, Frasheri D, Restifo N P, Rosenberg S A. Adoptive transfer of syngeneic T cells transduced with a chimeric antigen receptor that recognizes murine CD19 can eradicate lymphoma and normal B cells. Blood. 2010; 116:3875-3886.

Johnson L A, Morgan R A, Dudley M E et al. Gene therapy with human and mouse T-cell receptors mediates cancer regression and targets normal tissues expressing cognate antigen. Blood. 2009; 114:535-546.

Parkhurst M R, Yang J C, Langan R C et al. T cells targeting carcinoembryonic antigen can mediate regression of metastatic colorectal cancer but induce severe transient colitis. Mol Ther. 2011; 19:620-626.

Robbins P F, Morgan R A, Feldman S A et al. Tumor regression in patients with metastatic synovial cell sarcoma and melanoma using genetically engineered lymphocytes reactive with NY-ESO-1. J Clin Oncol. 2011; 29:917-924.

Peinert S, Prince H M, Guru P M et al. Gene-modified T cells as immunotherapy for multiple myeloma and acute myeloid leukemia expressing the Lewis Y antigen. Gene Ther. 2010; 17:678-686.

Xue S A, Gao L, Thomas S et al. Development of a Wilms' tumor antigen-specific T-cell receptor for clinical trials: engineered patient's T cells can eliminate autologous leukemia blasts in NOD/SCID mice. Haematologica. 2010; 95:126-134.

Brentjens R, Yeh R, Bernal Y, Riviere I, Sadelain M. Treatment of chronic lymphocytic leukemia with genetically targeted autologous T cells: case report of an unforeseen adverse event in a phase I clinical trial. Mol Ther. 2010; 18:666-668.

Zhang Z X, Yang L, Young K J, DuTemple B, Zhang L. Identification of a previously unknown antigen-specific regulatory T cell and its mechanism of suppression. Nat Med. 2000; 6:782-789.

Young K J, Kay L S, Phillips M J, Zhang L. Antitumor activity mediated by double-negative T cells. Cancer Res. 2003; 63:8014-8021.

Merims S, Li X, Joe B et al. Anti-leukemia effect of ex vivo expanded DNT cells from AML patients: a potential novel autologous T-cell adoptive immunotherapy. Leukemia. 2011; 25:1415-1422.

Young K J, DuTemple B, Phillips M J, Zhang L. Inhibition of graft-versus-host disease by double-negative regulatory T cells. J Immunol. 2003; 171:134-141.

He K M, Ma Y, Wang S et al. Donor double-negative Treg promote allogeneic mixed chimerism and tolerance. Eur J Immunol. 2007; 37:3455-3466.

McIver Z, Serio B, Dunbar A et al. Double-negative regulatory T cells induce allotolerance when expanded after allogeneic haematopoietic stem cell transplantation. Br J Haematol. 2008; 141:170-178.

Fontaine P, Roy-Proulx G, Knafo L, Baron C, Roy D C, Perreault C. Adoptive transfer of minor histocompatibility antigen-specific T lymphocytes eradicates leukemia cells without causing graft-versus-host disease. Nat Med. 2001; 7:789-794.

Barabe F, Kennedy J A, Hope K J, Dick J E. Modeling the initiation and progression of human acute leukemia in mice. Science. 2007; 316:600-604.

Ali N, Flutter B, Sanchez Rodriguez R, Sharif-Paghaleh E, Barber L D, Lombardi G, Nestle F O. Xenogeneic graft-versus-host-disease in NOD-scid IL-2Ry null mice display a T-effector memory phenotype. PLoS One. 2012; 7(8):e44219

Merims, S., P. Dokouhaki, B. Joe, and L. Zhang. 2011. Human Vd1-T cells regulate immune responses by targeting autologous immature dendritic cells. Hum. Immunol. 72: 32-36.

Kenderian, S. S. et al. CD33-specific chimeric antigen receptor T cells exhibit potent preclinical activity against human acute myeloid leukemia. Leukemia, doi:10.1038/leu.2015.52 (2015).

Lichtenegger, F. S., Krupka, C., Kohnke, T. & Subklewe, M. Immunotherapy for Acute Myeloid Leukemia. *Semin Hematol* 52, 207-214, doi:10.1053/j.seminhematol.2015.03.006 (2015).

Tettamanti, S., Biondi, A., Biagi, E. & Bonnet, D. CD123 AML targeting by chimeric antigen receptors: A novel magic bullet for AML therapeutics? *Oncoimmunology* 3, e28835, doi:10.4161/onci.28835 (2014).

Wang, Q. S. et al. Treatment of CD33-directed chimeric antigen receptor-modified T cells in one patient with relapsed and refractory acute myeloid leukemia. *Mol Ther* 23, 184-191, doi:10.1038/mt.2014.164 (2015).

Arpinati, M. & Curti, A. Immunotherapy in acute myeloid leukemia. *Immunotherapy* 6, 95-106, doi:10.2217/imt.13.152 (2014).

Campbell, K. S. & Hasegawa, J. Natural killer cell biology: an update and future directions. *The Journal of allergy and clinical immunology* 132, 536-544, doi:10.1016/j.jaci.2013.07.006 (2013).

Ruggeri, L. et al. Effectiveness of donor natural killer cell alloreactivity in mismatched hematopoietic transplants. *Science* 295, 2097-2100, doi:10.1126/science.1068440 (2002).

L Z June, C. H. (2007). "Adoptive T cell therapy for cancer in the clinic." *Journal of Clinical Investigation* 117(6): 1466-1476.

Hourigan, C. S. & Karp, J. E. Minimal residual disease in acute myeloid leukaemia. *Nat Rev Clin Oncol* 10, 460-471, doi:10.1038/nrclinonc.2013.100 (2013).

Brissot, E. & Mohty, M. Which Acute Myeloid Leukemia Patients Should Be Offered Transplantation? *Semin Hematol* 52, 223-231, doi:10.1053/j.seminhematol.2015.03.001 (2015).

Vyas, P., Appelbaum, F. R. & Craddock, C. Reprint of: Allogeneic hematopoietic cell transplantation for acute myeloid leukemia. *Biol Blood Marrow Transplant* 21, S3-10, doi:10.1016/j.bbmt.2014.12.032 (2015).

MacDonald, K. P., Shlomchik, W. D. & Reddy, P. Biology of graft-versus-host responses: recent insights. *Biol Blood Marrow Transplant* 19, S10-14, doi:10.1016/j.bbmt.2012.11.005 (2013).

McDermott, S. P., Eppert, K., Lechman, E. R., Doedens, M. & Dick, J. E. Comparison of human cord blood engraftment between immunocompromised mouse strains. *Blood* 116, 193-200, doi:10.1182/blood-2010-02-271841 (2010).

Drake, A. C. et al. Human CD34+ CD133+ hematopoietic stem cells cultured with growth factors including Angptl5 efficiently engraft adult NOD-SCID Il2rgamma−/− (NSG) mice. *PLoS One* 6, e18382, doi:10.1371/journal.pone.0018382 (2011)

Covassin, L. et al. Human peripheral blood CD4 T cell-engrafted non-obese diabetic-scid IL2rgamma(null) H2-Ab1 (tm1Gru) Tg (human leucocyte antigen D-related 4) mice: a mouse model of human allogeneic graft-versus-host disease. *Clin Exp Immunol* 166, 269-280, doi: 10.1111/j.1365-2249.2011.04462. (2011).

The invention claimed is:

1. A method of treating leukemia or lymphoma in a subject in need thereof, comprising administering to the subject an effective amount of double negative T cells (DNTs) and a cell cycle inhibitor, wherein the DNTs are mature allogenic DNTs that have been expanded in vitro.

2. The method of claim 1, wherein the leukemia is acute myeloid leukemia (AML).

3. The method of claim 1, wherein the DNTs are from one or more subjects without cancer.

4. The method of claim 1, wherein the DNTs are obtained from a sample comprising peripheral blood mononuclear cells (PBMC).

5. The method of claim 1, wherein the subject has recurrent, relapsing or refractory AML.

6. The method of claim 5, wherein the recurrent or relapsing AML is caused by minimal residual disease (MRD) or leukemic stem cells.

7. The method of claim 1, further comprising administering to the subject one or more additional doses of an effective amount of DNTs.

8. The method of claim 1, wherein the cell cycle inhibitor is AraC.

9. The method of claim 1, comprising administering the DNTs to the subject prior to the cell cycle inhibitor.

10. The method of claim 1, comprising administering the DNTs to the subject at the same time as the cell cycle inhibitor.

11. The method of claim 1, comprising administering the DNTs to the subject after the cell cycle inhibitor.

12. The method of claim 1, comprising administering the DNTs to the subject within 3 weeks of the cell cycle inhibitor.

13. The method of claim 1, comprising administering the DNTs to the subject within 2 weeks of the cell cycle inhibitor.

14. The method of claim 1, comprising administering the DNTs to the subject within 1 week of the cell cycle inhibitor.

15. The method of claim 11, comprising administering the DNTs to the subject between 2 days and 7 days after the cell cycle inhibitor.

16. The method of claim 1, wherein the cell cycle inhibitor is Doxorubicin, Melphlan, Roscovitine, Mitomycin C, Hydroxyurea, 50Fluorouracil, Cisplatin, Arabinofuranosyl Cytidine (AraC), Etoposide, Gemcitabine, Bortezomib, Sunitinib, Sorafenib, Sodium Valproate, FR01228, Trichostatin A, SAHA, PDX101, or Dacarbazine.

17. The method of claim 1, wherein the cell cycle inhibitor is a DNA synthesis inhibitor selected from AraC (cytarabine), 6-mercaptopurine, 6-thioguanine, 5-fluorouracil, capecitabine, floxuridine, gemcitabine, decitabine, vidaza, fludarabine, nelarabine, cladribine, clofarabine, pentostatin, thiarabine, troxacitabine, sapacitabine and forodesine.

18. The method of claim 1, wherein the cell cycle inhibitor is a DNA elongation terminator selected from cytarabine, fludarabine, nelarabine, cladribine, and clofarabine.

19. The method of claim 1, wherein the leukemia or lymphoma in the subject is chemotherapy resistant leukemia or lymphoma.

20. The method of claim 1, wherein the DNTs express a Chimeric Antigen Receptor (CAR) that preferentially binds to a leukemic cell or a lymphoma cell.

* * * * *